United States Patent
Watanabe

(10) Patent No.: US 10,959,628 B2
(45) Date of Patent: Mar. 30, 2021

(54) BIOLOGICAL INFORMATION DETECTION DEVICE USING SECOND LIGHT FROM TARGET ONTO WHICH DOTS FORMED BY FIRST LIGHT ARE PROJECTED

(71) Applicant: Panasonic Intellectual Property Management Co., Ltd., Osaka (JP)

(72) Inventor: Hisashi Watanabe, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 0 days.

(21) Appl. No.: 16/845,708

(22) Filed: Apr. 10, 2020

(65) Prior Publication Data

US 2020/0237238 A1 Jul. 30, 2020

Related U.S. Application Data

(62) Division of application No. 15/628,679, filed on Jun. 21, 2017, now Pat. No. 10,653,328.

(30) Foreign Application Priority Data

Jun. 30, 2016 (JP) .................. 2016-130137

(51) Int. Cl.
*A61B 5/026* (2006.01)
*G06K 9/20* (2006.01)
(Continued)

(52) U.S. Cl.
CPC .......... *A61B 5/0261* (2013.01); *A61B 5/0077* (2013.01); *A61B 5/021* (2013.01);
(Continued)

(58) Field of Classification Search
None
See application file for complete search history.

(56) References Cited

U.S. PATENT DOCUMENTS 6,859,658 B1  2/2005  Krug
9,940,710 B2 * 4/2018  Watanabe ............. G06T 7/0012
(Continued)

FOREIGN PATENT DOCUMENTS

JP   H06-054836 A   3/1994
JP   2002-200050 A  7/2002
(Continued)

OTHER PUBLICATIONS

Hirooki Aoki et al., "Non-contact and Unrestrained Respiration Watch System for Sleeping Person Using Near-Infrared Bright Spots Matrix Irradiation", IEEJ Transactions on Electrical and Electronic Engineering, C. Electronics, Information and Systems, Jun. 1, 2004, vol. 124(6), pp. 1251-1258.
(Continued)

*Primary Examiner* — Tahmina N Ansari
(74) *Attorney, Agent, or Firm* — McDermott Will & Emery LLP

(57) ABSTRACT

A biological information detection device includes a light source, an image capturing device, and one or more arithmetic circuits. The light source projects dots formed by light onto a target including a living body. The image capturing device includes photodetector cells and generates an image signal representing an image of the target onto which the dots are projected. The one or more arithmetic circuits detect a portion corresponding to at least a part of the living body in the image by using the image signal and calculate biological information of the living body by using image signal of the portion.

20 Claims, 31 Drawing Sheets

(51) Int. Cl.
*H04N 9/083* (2006.01)
*A61B 5/00* (2006.01)
*A61B 5/16* (2006.01)
*G06K 9/00* (2006.01)
*H04N 9/04* (2006.01)
*A61B 5/021* (2006.01)
*A61B 5/1455* (2006.01)
*H04N 5/33* (2006.01)
*H04N 13/239* (2018.01)

(52) U.S. Cl.
CPC .......... *A61B 5/14552* (2013.01); *A61B 5/165* (2013.01); *A61B 5/441* (2013.01); *A61B 5/443* (2013.01); *A61B 5/444* (2013.01); *A61B 5/445* (2013.01); *A61B 5/7207* (2013.01); *A61B 5/7278* (2013.01); *G06K 9/00362* (2013.01); *G06K 9/00906* (2013.01); *G06K 9/2036* (2013.01); *H04N 9/04557* (2018.08); *A61B 2562/0233* (2013.01); *A61B 2576/00* (2013.01); *G06K 9/00281* (2013.01); *G06K 2009/00932* (2013.01); *H04N 5/33* (2013.01); *H04N 9/045* (2013.01); *H04N 9/083* (2013.01); *H04N 13/239* (2018.05)

(56) References Cited

U.S. PATENT DOCUMENTS

| | | | |
|---|---|---|---|
| 2013/0023966 A1* | 1/2013 | Depfenhart | A61B 18/203 607/89 |
| 2013/0329031 A1* | 12/2013 | Miura | G06K 9/2018 348/77 |
| 2014/0303454 A1* | 10/2014 | Clifton | G06T 5/008 600/301 |
| 2016/0022181 A1 | 1/2016 | Valsan et al. | |

FOREIGN PATENT DOCUMENTS

| JP | 2003-517342 A | 5/2003 |
|---|---|---|
| JP | 2004-167080 A | 6/2004 |
| JP | 2005-218507 A | 8/2005 |
| JP | 2008-237244 A | 10/2008 |
| JP | 2014-527863 A | 10/2014 |
| JP | 2016-002164 A | 1/2016 |
| JP | 2016-030214 A | 3/2016 |

OTHER PUBLICATIONS

Tsutomu Kuroda et al., "Analysis of facial color and skin temperature in emotional change and its synthesis of facial color", Human Interface Society, vol. 1 No. 1, pp. 15-20, Feb. 16, 1999.
Non-final Office Action dated Apr. 30, 2019 in U.S. Appl. No. 15/628,679.
Final Office Action dated Sep. 18, 2019 in U.S. Appl. No. 15/628,679.
Notice of Allowance dated Jan. 13, 2020 in U.S. Appl. No. 15/628,679.
Tomoaki Ueda, "Kinect Changes the World of Sensing", Jan. 25, 2013, Search Date: Apr. 14, 2020, URL, http://www.neo-tech.lab.jp/ARsensing/#MovieNews10, with partial translation.

* cited by examiner

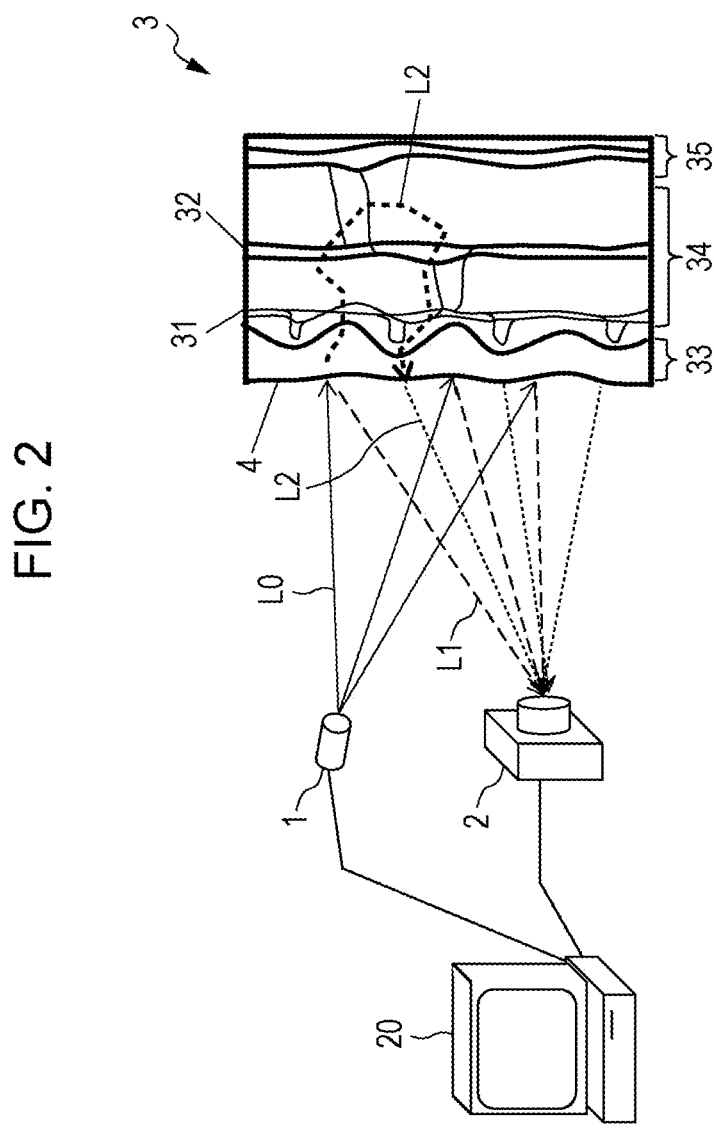

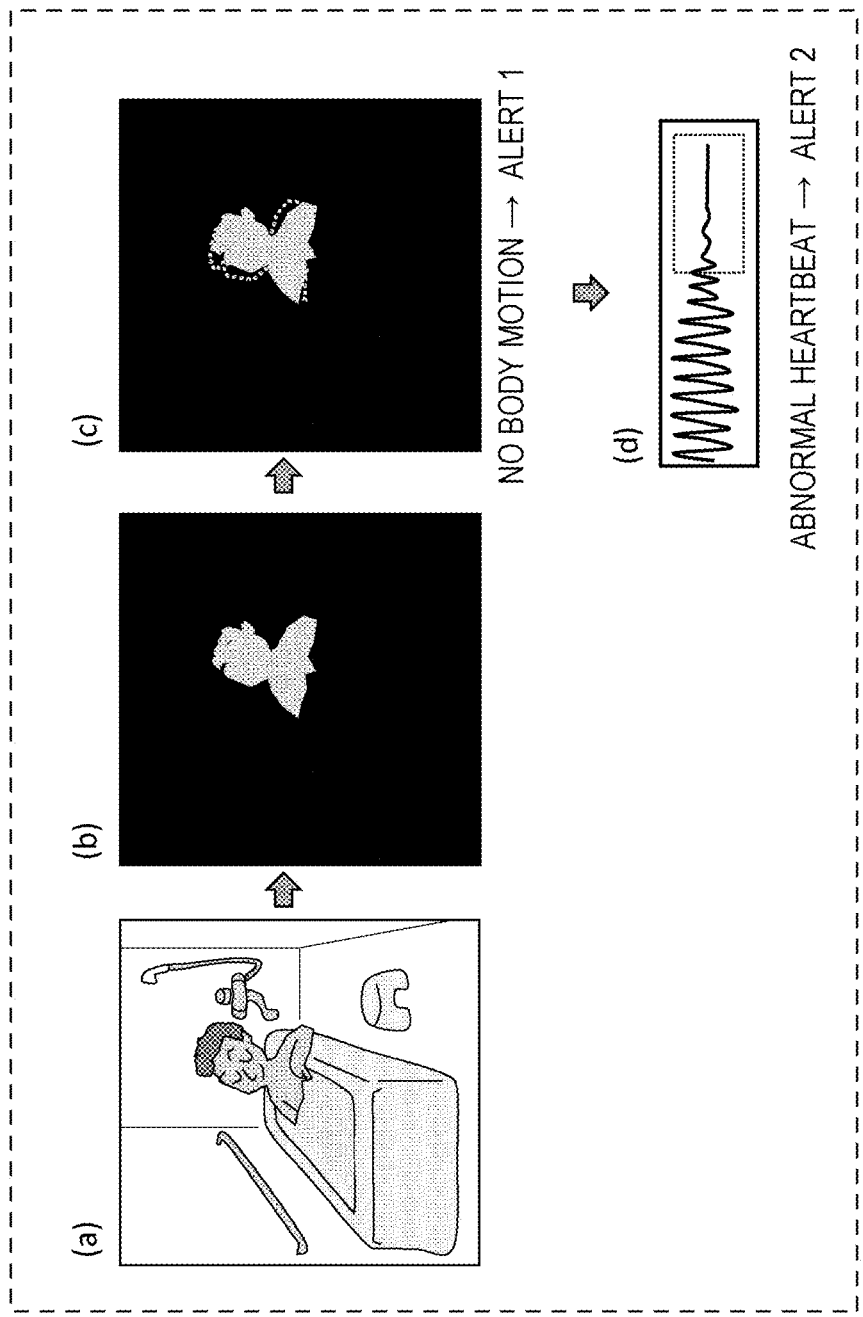

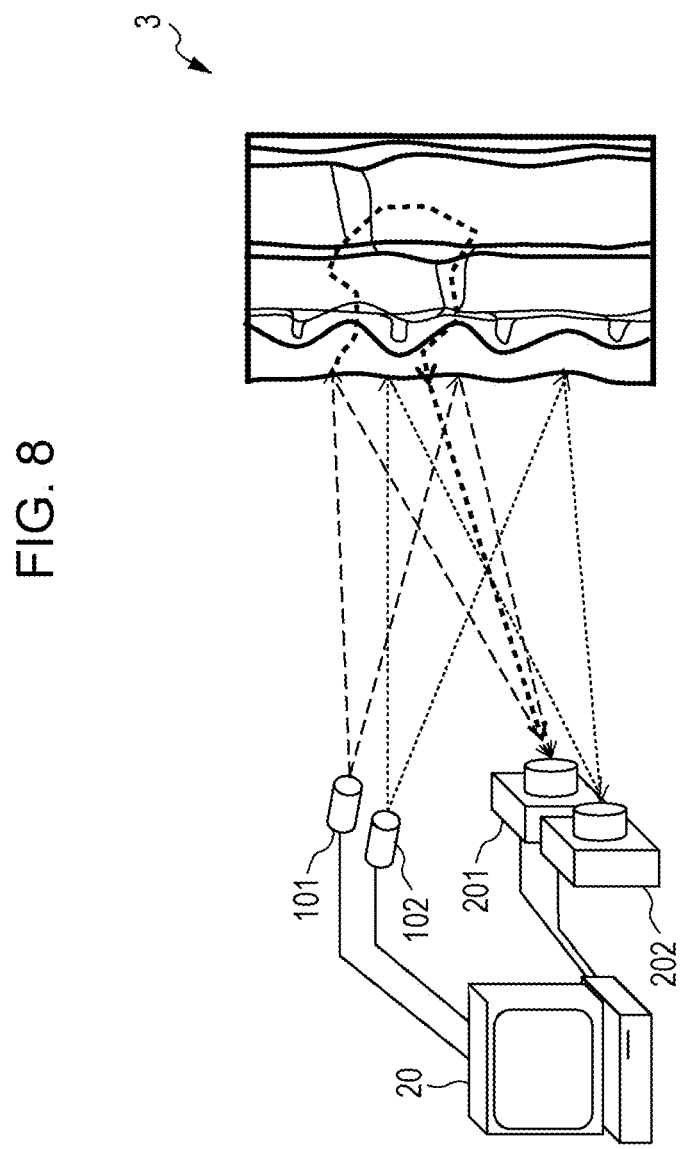

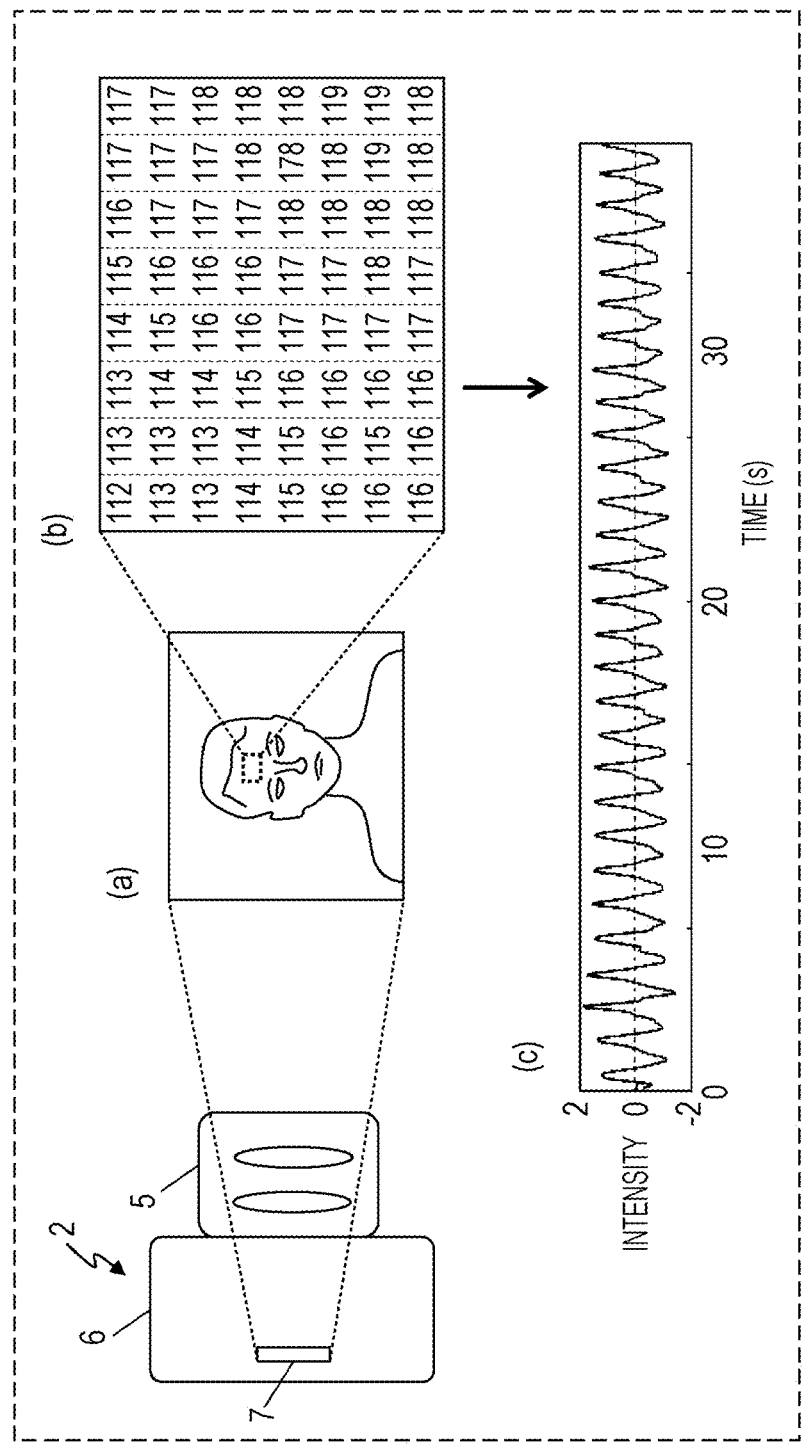

BIOLOGICAL INFORMATION DETECTION DEVICE USING SECOND LIGHT FROM TARGET ONTO WHICH DOTS FORMED BY FIRST LIGHT ARE PROJECTED

This application is a Divisional Application of U.S. patent application Ser. No. 15/628,679, filed on Jun. 21, 2017, which claims the benefit of Japanese Application No. 2016-130137, filed on Jun. 30, 2016, the disclosures of which are incorporated herein by reference.

BACKGROUND

1. Technical Field

The present disclosure relates to biological information detection devices. The present disclosure relates to, for example, a biological information detection device that detects biological information, such as heartbeat, in a non-contact manner.

2. Description of the Related Art

Heartbeat, blood flow, blood pressure, blood oxygen saturation, etc. are widely used as basic parameters for determining the health condition of a person. These pieces of biological information relating to blood are typically measured by using contact-type measuring instruments. Since contact-type measuring instruments are attached to the body of a subject, measurement, especially, long continuous measurement, sometimes incurs the subject's discomfort.

Various attempts have been made to easily obtain basic biological information for determining the health condition of a person through measurement. For example, Japanese Unexamined Patent Application Publication No. 2005-218507 discloses a method for detecting heart rate in a non-contact manner on the basis of image information of a face or the like obtained with a camera. Japanese Unexamined Patent Application Publication (Translation of PCT Application) No. 2003-517342 discloses a method for measuring, using a white light source and a laser light source, blood oxygen saturation on the basis of a laser Doppler effect of laser light scattered behind the surface of a living body. Japanese Unexamined Patent Application Publication (Translation of PCT Application) No. 2014-527863 discloses a method for measuring, using an ordinary color camera, blood oxygen saturation while removing the influence of ambient light.

SUMMARY

In one general aspect, the techniques disclosed here feature a biological information detection device including a first light source, an image capturing device, and one or more arithmetic circuits. The first light source, in operation, projects first dots onto a target including a living body. The first dots are formed by first light. The image capturing device, in operation, generates and outputs a first image signal representing a first image of the target onto which the first dots are projected. The image capturing device includes first photodetector cells that, in operation, detect second light returning from the target onto which the first dots are projected. The one or more arithmetic circuits, in operation, detect a first portion corresponding to at least a part of the living body in the first image by using the first image signal and calculate biological information of the living body by using image signal of the first portion.

It should be noted that general or specific embodiments may be implemented as an element, a device, a system, a method, an integrated circuit, a computer program, a recording medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 2 is a diagram illustrating a configuration of a biological information detection device according to a first embodiment;

FIG. 7B is a diagram for explaining an algorithm of a watch system in accordance with the third embodiment;

FIG. 8 is a diagram illustrating a configuration of a biological information detection device according to a fourth embodiment;

FIG. 21 is a diagram illustrating an example (comparative example) of a configuration of a biological information sensing system using an image capturing device.

DETAILED DESCRIPTION

Figure 1A:
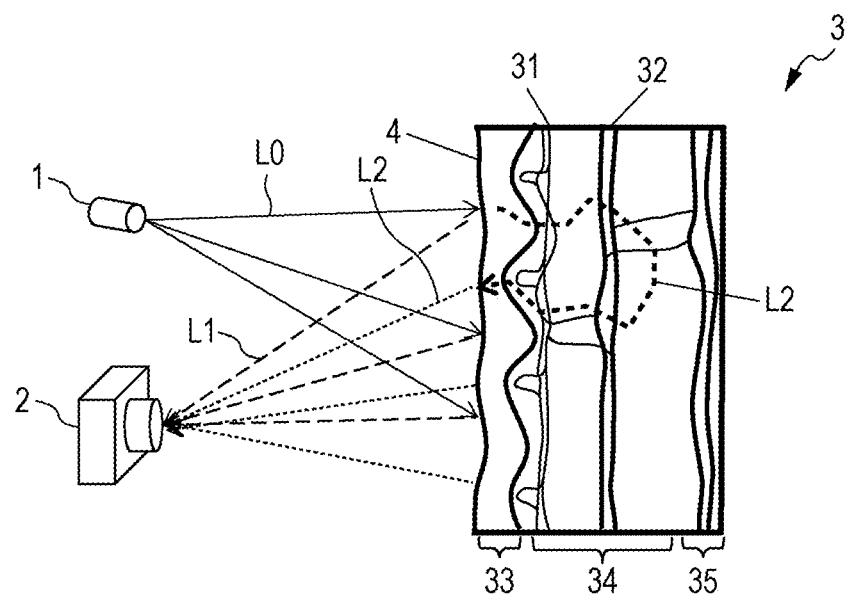
FIG. 1A is a diagram for explaining a basic concept of how biological information is obtained in accordance with an embodiment of the present disclosure.

Prior to description of embodiments of the present disclosure, underlying knowledge forming the basis of the present disclosure will be described.

Since remote biological information sensing with a camera enables long continuous measurement without causing the subject to feel constrained, various applications of such remote biological information sensing are anticipated. For example, at medical facilities such as hospitals, applications such as constantly monitoring the condition of a patient and quickly dealing with a sudden change in condition and utilizing data obtained by long-time monitoring to make a diagnosis are anticipated. Not only utilization of remote biological information sensing at medical facilities but also utilization thereof at home to prevent sudden death during sleep and to monitor patients having sleep apnea syndrome are anticipated. Further, an application in which a change in the physical condition is constantly monitored by constantly obtaining physical information data in daily life at home or at work and analyzing data accumulated in a server via a cloud network and the analysis result is used for health management and an application in which the obtained data is shared among medical facilities and is used for medical treatment are also anticipated. To constantly obtain such biological information, systems that constantly obtain biological information without causing a subject to feel constrained and without being noticed by the subject are desired. Systems using cameras enable non-constrained remote measurement and thus are considered to be optimum for such applications.

However, the privacy needs to be considered when biological information sensing is performed by using cameras in daily life. Since systems in which high-resolution images that enable identification of individuals imaged with cameras are stored in a storage device involve a risk of image leakage, such systems need to be avoided. Even in the case where obtained images are not stored, systems in which cameras (or camera lenses) are seen from a measurement system can make the subject psychologically uncomfortable. Accordingly, systems with hidden cameras are desirable.

Systems for implementing remote biological information sensing by using cameras have been developed by various research facilities in response to the above-described strong demand in the medical and healthcare fields, and some products are now commercially available. The biggest challenge of remote biological information sensing systems of the related art that use cameras lies in the accuracy and stability of measurement. In the case where images of the human body are captured with a camera, most of the light incident on the camera is light reflected from the skin surface or a portion close to the skin surface. Since there are no blood vessels and no metabolism occurs at the stratum corneum, which is the outermost layer of the skin, no biological information is obtained from surface reflected components. It is necessary to detect light that has reached the inner portion of the skin and has been reflected from an epidermal portion where blood vessels are present. The component reflected from the skin surface is dominant in light reflected from the skin, and light that has reached the inner portion of the skin is rapidly lost by strong light absorption of a living body. Accordingly, the ratio of light containing biological information to the reflected light is low. Further, systems that do not include an illumination system for measurement and that capture images by using ambient light has an issue of instability that is caused by a fluctuation in an obtained image signal due to a fluctuation in ambient light.

Further, in the case of remote sensing, the instability of measurement due to a body motion is a big issue. Since an obtained signal varies due to a change in a measurement region and a change in direction (angle) toward the camera in response to body motion, stable measurement is difficult to perform. As described before, most of the signal obtained with a camera is a component resulting from reflection from the skin surface which does not contain biological information, and a signal component containing biological information is weak. Since the reflection from the surface greatly changes because of changes in the measurement region and in the direction due to a body motion, weak biological information is not successfully obtained. This is the biggest challenge of remote biological information sensing using cameras. It is necessary to perform measurement in a stationary state by holding the body still, and a benefit of not being constrained is not fully provided.

Since images of a subject are obtained in remote biological information sensing using cameras, methods for reducing the influence of a body motion by using these images are used in some cases. In such methods, a face portion is detected by using a face recognition function from images obtained with a camera, a portion subjected to measurement is further recognized by performing face part recognition, and biological information is detected by constantly capturing an image of the portion subjected to measurement even if there is a body motion. For example, if a forehead portion is successfully detected by face part recognition, information relating to the forehead portion is successfully obtained constantly even if the forehead portion moves in the images due to a body motion.

However, the methods using image recognition have two issues. One is that computation load is heavy because face parts are recognized by performing feature extraction on the entire image. Thus, it is necessary to perform fast image processing by using an expensive high-performance arithmetic unit or it is necessary to reduce frame rate of an image capturing device so that the next frame can be processed after processing of one frame is finished. Fast processing is costly and results in a larger and more expensive device. When slow processing is employed, the measurement accuracy decreases. Another issue is that even if the influence of a body motion is reduced by performing image recognition, the increase in detection accuracy is limited due to a change in the direction of a subject portion (angle of direction of a normal to the surface of the subject portion with respect to the frontal direction of the camera) in response to a body motion. The reflectance of surface reflected light is angle-dependent. Accordingly, an amount of surface reflected light that reaches the camera varies when the direction of the measurement-target portion changes due to a body motion. Consequently, the detection accuracy decreases.

As described above, the biggest challenge of remote biological information sensing performed using cameras is the instability of measurement due to a body motion. Because of low reliability resulting from this instability, remote biological information sensing using cameras has not been used for various applications.

As described above, various attempts have been made to obtain basic biological information for determining the health condition of a person through measurement. For example, a method for detecting heart rate in a non-contact manner on the basis of image information of a face or the like obtained with a camera has been proposed in Japanese Unexamined Patent Application Publication No. 2005-218507. In the method according to Japanese Unexamined Patent Application Publication No. 2005-218507, heart rate is determined by analyzing a spatial frequency component of an obtained color image. However, since the accuracy achieved by this method decreases due to the influence of disturbance light, such as light illuminating a room, stable detection is difficult.

Pulse oximeters are commonly used to measure blood oxygen saturation. Pulse oximeters radiate two wavelengths of light in a red to near-infrared wavelength range onto a finger inserted therein and measure transmittance of the light. In this way, pulse oximeters are capable of determining a ratio between an oxyhemoglobin concentration and a deoxyhemoglobin concentration in blood. Pulse oximeters are capable of measuring blood oxygen saturation with a simple configuration. However, since pulse oximeters are contact-type devices, they may make people feel restrained.

Japanese Unexamined Patent Application Publication (Translation of PCT Application) No. 2003-517342 discloses an example of a non-contact-type blood oxygen saturation measuring device. This device measures, by using a white light source and a laser light source, blood oxygen saturation on the basis of a laser Doppler effect of laser light scattered behind the surface of a living body. This method, however, makes a configuration of the device complex, and the resulting signal is weak.

In Japanese Unexamined Patent Application Publication (Translation of PCT Application) No. 2014-527863, a method for measuring, by using an ordinary color camera, blood oxygen saturation while removing the influence of ambient light has been proposed. Since this method is greatly influenced by reflected light reflected from the surface of skin, it is difficult to measure blood oxygen saturation stably at a high accuracy.

As described above, the non-contact-type measurement methods for measuring biological information, such as heart rate, blood pressure, or blood oxygen saturation of the related art have issues related to the accuracy and the stability.

To measure biological information by using a camera, it is necessary to locate a measurement-target region (e.g., a forehead region) in images obtained with a camera and to detect biological information by using image information in the region. Types of the method for locating the measurement-target region include a method in which the measurement-target region is specified before measurement and a method in which the measurement-target region is automatically set based on images. In the method in which the measurement-target region is specified before measurement, a person who carries out the measurement specifies the measurement-target region based on an image of a subject before starting the measurement and continuously performs measurement at the same portion during the measurement. This method is simple but does not allow the subject to move during the measurement. Accordingly, a benefit of non-contact measurement, which is not being constrained, is lost. To avoid this, the method in which the measurement-target region is automatically set is sometimes used. In this method, for example, when the measurement-target region is a forehead region, the camera performs face recognition on each obtained image and further performs face part recognition to locate the forehead portion in the image. Then, measurement can be performed at that portion.

FIG. 21 is a diagram schematically illustrating an example (comparative example) of such a system. An image capturing device 2, which is a camera of this system, includes a camera casing 6 including an image sensor 7, and an optical system 5 including lenses. The image sensor 7 of the image capturing device 2 includes or is connected to an arithmetic unit (or arithmetic circuit). The arithmetic unit performs face recognition on each obtained image (e.g., part (a) of FIG. 21) and extracts pieces of image data of a forehead portion (e.g., part (b) of FIG. 21) after locating the forehead portion. The arithmetic unit then generates biological information, such as a change in heartbeat (e.g., part (c) of FIG. 21), from the pieces of image data of the forehead portion. Part (c) of FIG. 21 illustrates a temporal change in the average of the pieces of image data of the forehead portion illustrated in part (b) of FIG. 21 in the region of the forehead portion. A face part recognition algorithm used in this system imposes heavy load on the computer performing the image processing. Accordingly, the cost of the arithmetic unit increases to implement fast processing. In addition, the method using image recognition has an issue in that the recognition accuracy decreases when the orientation of the body changes or when part of the face is hidden. The method using image recognition further has an issue in that it is easily affected by ambient light. For these reasons, it is difficult to continuously perform stable measurement.

In addition to the issues described above, the method using face recognition also has an issue in that measurement is not successfully performed at a portion (such as an arm or chest) other than the face. Further, it involves an issue regarding consideration for the privacy. The subject is psychologically stressed out by constant image capturing with a camera. However, highly accurate image recognition requires the use of a high-resolution camera for image capturing. Accordingly, constant image capturing with a camera may impose psychological load on the subject.

The inventor has focused on the above-described issues and has studied a configuration for addressing the issues. The inventor consequently has found out that the issues can be addressed by obtaining an image by using a light source that projects a light dot pattern onto the surface of a living body, by detecting a living body region (e.g., a human body region) in the image on the basis of a ratio between a component relating to directly reflected light (also referred to as "surface reflected light") and a component relating to scattered light scattered inside the living body (referred to as "inside body scattered light") in the image, and by separating, through signal processing, the component relating to the directly reflected light from the component relating to the inside body scattered light in the detected living body region. That is, a biological information detection device first detects a region that is estimated to be a living body in an image and obtains biological information in that region. Such a method can greatly reduce an amount of computation relating to image processing and enables fast and stable biological information detection as described in detail below.

A biological information detection device according to an aspect of the present disclosure includes a first light source, an image capturing device, and one or more arithmetic circuits. The first light source, in operation, projects first dots onto a target including a living body. The first dots are formed by first light. The image capturing device, in operation, generates and outputs a first image signal representing a first image of the target onto which the first dots are projected. The image capturing device includes first photodetector cells that, in operation, detect second light returning from the target onto which the first dots are projected. The one or more arithmetic circuits, in operation, detect a first portion corresponding to at least a part of the living body in the first image by using the first image signal and calculate biological information of the living body by using image signal of the first portion.

The first arithmetic circuit successfully detects a living body region on the basis of a ratio between a signal of pixels in a region onto which the dot pattern is projected and a signal of pixels in an adjacent region of the region. For example, the first arithmetic circuit is capable of determining whether a living body is present at a position corresponding to a specific pixel of the image on the basis of a ratio (referred to as contrast) between a standard deviation of a pixel value of the specific pixel and pixel values of a plurality of pixels located adjacent to the specific pixel and an average of the pixel value of the specific pixel and the pixel values of the plurality of pixels located adjacent to the specific pixel. The second arithmetic circuit generates and outputs information concerning the living body by mainly using a signal relating the region in which the dot pattern is not projected out of the image signal. With such a configuration, biological information is successfully obtained at a high accuracy.

Herein, the term "biological information" refers to various kinds of information relating to a living body, such as heart rate, blood flow, blood pressure, blood oxygen saturation, and respiratory information. Herein, the term "biological information" also refers to information indicating the state of a person, such as the concentration degree or an emotion of a person, which is determined from these pieces of information.

Principle

A principle allowing a biological information detection device to obtain highly accurate biological information will be described below.

Biological information detection devices according to embodiments of the present disclosure use light having a wavelength in a range from approximately 650 nm to approximately 950 nm. This wavelength range is within a wavelength range of red to near-infrared light. Herein, the term "light" is used not only for visible light but also for infrared. The above wavelength range is called "optical tissue window" and is known as a range in which absorbance in the body is low.

Figure 22:
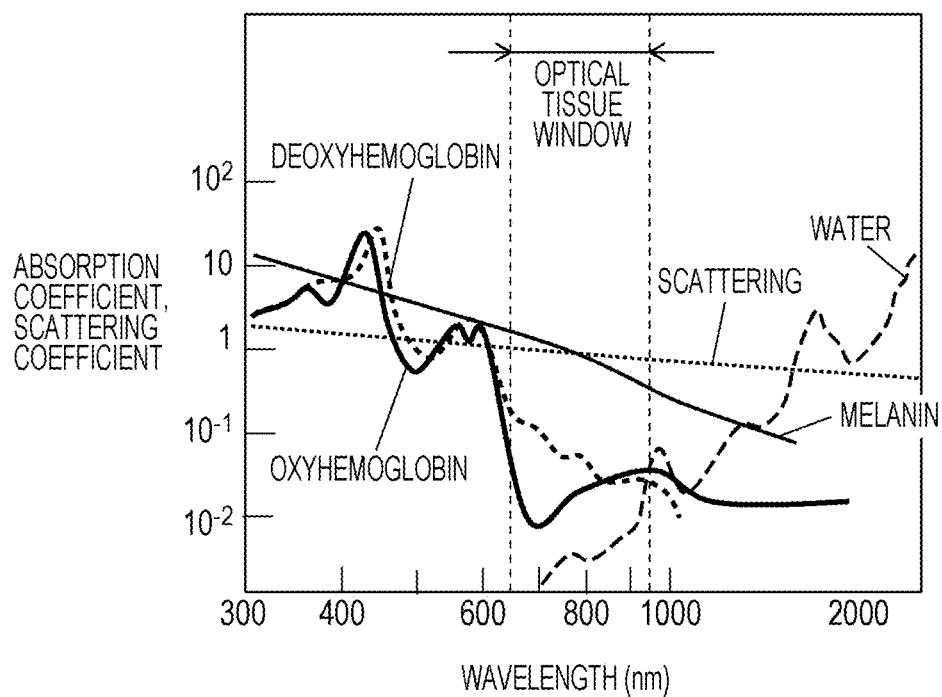
FIG. 22 is a diagram illustrating absorption coefficients and scattering coefficients of hemoglobin, melanin, and water, which are main components of a living body, in a wavelength range from visible light to near-infrared light

FIG. 22 is a diagram illustrating wavelength dependency of a light absorption coefficient and an inside-body light scattering coefficient for each of oxyhemoglobin, deoxyhemoglobin, melanin, and water. Light in a visible light range of 650 nm or shorter is absorbed mainly by blood (i.e. hemoglobin), and light in a wavelength range longer than 950 nm is absorbed mainly by water. Therefore, light in these wavelength ranges is not suitable for obtaining biological information. In contrast, in a wavelength range from approximately 650 nm to approximately 950 nm, the absorption coefficients for hemoglobin and water are relatively low, and the scattering coefficient is relatively high. The scattering coefficient is larger than the absorption coefficient by an order of magnitude or more, and scattering is dominant in the wavelength band of "optical tissue window" in terms of interaction between the skin and near-infrared light. Therefore, light of this wavelength range returns to the body surface after entering the body and being strongly scattered. Since such optical characteristics are unique to the skin, the use of these scattering-reflection characteristics allows the human body to be distinguished from other substances.

Biological information detection devices according to embodiments of the present disclosure mainly utilize light of this wavelength range corresponding to the "optical tissue window". Since the use of a dot array light source, for example, enables spatial separation and detection of light directly reflected from the living-body surface and returning light that has been scattered inside the living body, biological information can be efficiently obtained.

FIG. 1A is a diagram illustrating a schematic configuration of a biological information detection device according to an illustrative embodiment of the present disclosure. The biological information detection device includes a light source 1 and an image capturing device 2, which is a camera. The light source 1 is an array point light source that projects a plurality of discretely arranged points (also referred to as "arrayed points" or "dot pattern" herein) onto a target including a living body 3. The light source 1 is arranged such that a plurality of points are projected onto the living body 3. The image capturing device 2 includes an image sensor (also referred to as an "imaging element"), captures an image of a living-body surface 4, and generates and outputs an image signal.

Figure 1B:
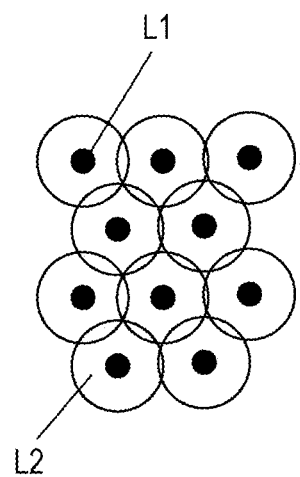
FIG. 1B is a diagram for explaining characteristics of an image of the surface of a living body, obtained with an image capturing device.

FIG. 1B is a diagram for explaining characteristics of the image of the living-body surface 4, obtained by the image capturing device 2. Outgoing light L0 from the light source 1 is reflected by the living-body surface 4. Surface reflected light L1 reflected by the living-body surface 4 maintains an image of the arrayed points formed by the light source 1. In contrast, inside-body scattered light L2 that exits from the living-body surface 4 after entering the living body 3 and being scattered inside the living body 3 no longer maintains the image of the arrayed points formed by the light source 1 because of strong scattering that occurs inside the living body 3. The use of the light source 1 allows the surface reflected light L1 and the inside-body scattered light L2 to be spatially separated from each other easily.

The living body 3 illustrated in FIG. 1A represents human skin and includes epidermis 33, dermis 34, and a subcutaneous tissue 35. No blood vessels are present at the epidermis 33, whereas capillaries 31 and arterioles/venules 32 are located at the dermis 34. Since there are no blood vessels at the epidermis 33, the surface reflected light L1 does not contain information relating to blood. Since the epidermis 33 includes melanin that strongly absorbs light, the surface reflected light L1 reflected from the epidermis 33 becomes noise when blood-related information is obtained. Thus, the surface reflected light L1 is not only useless to obtain blood-related information but also disturbs acquisition of accurate blood-related information. To detect biological information at a high accuracy, it is extremely important to suppress the influence of the surface reflected light and to efficiently obtain information of the inside-body scattered light.

To address the issues described above, embodiments of the present disclosure have a novel configuration with which directly reflected light and inside-body scattered light are spatially separated by using a light source that projects arrayed points onto a living body and an image capturing device (or an image capturing system). With this novel configuration, information concerning the living body can be measured at a high accuracy in a non-contact manner.

In the related art, methods using polarizing illumination such as the one disclosed in Japanese Unexamined Patent Application Publication No. 2002-200050 have been used to separate directly reflected light reflected from the living-body surface. In such methods using polarizing illumination, a polarizer having a polarized light transmission axis perpendicular to a polarization direction of illuminating light reflected from an image-capturing target is used. The influence of surface reflected light can be suppressed by capturing an image with a camera through such a polarizer. However, since the degree of polarization of surface reflected light reflected from an uneven surface such as skin changes depending on the position, separation of such directly reflected light is not sufficient. With a method according to embodiments of the present disclosure, the influence of surface reflected light can be suppressed more effectively because directly reflected light and scattered light are successfully spatially separated.

The present disclosure includes, for example, aspects recited in the following items.

[Item 1] In accordance with Item 1 of the present disclosure, a biological information detection device includes a first light source, an image capturing device, and one or more arithmetic circuits. The first light source, in operation, projects first dots onto a target including a living body. The first dots are formed by first light. The image capturing device, in operation, generates and outputs a first image signal representing a first image of the target onto which the first dots are projected. The image capturing device includes first photodetector cells that, in operation, detect second light returning from the target onto which the first dots are projected. The one or more arithmetic circuits, in operation, detect a first portion corresponding to at least a part of the living body in the first image by using the first image signal and calculate biological information of the living body by using image signal of the first portion.

[Item 2] In the biological information detection device according to Item 1, the second light may include third light from a first position on a surface of the target and fourth light from a second position on the surface of the target, the first position being a position onto which at least one first dot among the first dots is projected, and the second position being a position that is different from any of positions onto which the first dots are projected and that is located around the first position, the one or more arithmetic circuits may, in operation, detect the first portion in the first image by using a first image signal component corresponding to the third light and a second image signal component corresponding to the fourth light, the first image signal component and the second image signal component being contained in the first image signal, and the one or more arithmetic circuits may, in operation, calculate the biological information of the living body by using image signal of the second position in the first portion.

[Item 3] In the biological information detection device according to Item 2, the one or more arithmetic circuits may, in operation, determine a ratio between intensity of the first image signal component and intensity of the second image signal component and may, in operation, detect the first portion of the first image by using the ratio.

[Item 4] In the biological information detection device according to Item 2, the one or more arithmetic circuits may, in operation, detect the first portion of the first image by using ratios between a standard deviation and an average of intensity of the first image signal component and a standard deviation and an average of intensity of the second image signal component.

[Item 5] In the biological information detection device according to any one of Items 1 to 4, the first light may include light having a wavelength that is greater than or equal to 650 nm and less than or equal to 950 nm.

[Item 6] In the biological information detection device according to any one of Items 1 to 5, the biological information may include at least one piece of information selected from the group consisting of heart rate of the living body, blood pressure of the living body, blood flow of the living body, blood oxygen saturation of the living body, melanin concentration at skin of the living body, presence or absence of a spot at skin of the living body, and presence or absence of a bruise at skin of the living body.

[Item 7] In the biological information detection device according to any one of Items 1 to 6, the image capturing device may further include
a first bandpass filter that passes the second light, and an image sensor having an imaging surface on which the first photodetector cells are disposed and on which light that has passed through the first bandpass filter is incident.

[Item 8] In the biological information detection device according to any one of Items 1 to 7, the one or more arithmetic circuits may, in operation, calculate, as the biological information, at least one piece of information selected from the group consisting of heart rate of the living body, blood pressure of the living body, and blood flow of the living body by using a temporal change in a value obtained by performing lowpass filtering processing on at least part of the image signal of the first portion.

[Item 9] The biological information detection device according to any one of Items 1 to 8, may further include a second light source that, in operation, projects second dots onto the target, the second dots being formed by fifth light, wherein:

the first light may include light having a waveform that is greater than or equal to 650 nm and less than or equal to 800 nm, the fifth light may include light having a waveform that is greater than or equal to 800 nm and less than or equal to 950 nm, the image capturing device may further include second photodetector cells that, in operation, detect sixth light from the target onto which the second dots are projected, and the image capturing device may, in operation, generate and output a second image signal representing a second image of the target onto which the second dots are projected.

[Item 10] In the biological information detection device according to Item 9, the image capturing device may further include an image sensor having an imaging surface that is divided into a first region in which the first photodetector cells are disposed and a second region in which the second photodetector cells are disposed, a first optical system that, in operation, forms the first image in the first region, and a second optical system that, in operation, forms the second image in the second region.

[Item 11] In the biological information detection device according to Item 10, the image capturing device may further include a first bandpass filter that is disposed in a path of the second light and that passes the second light, and a second bandpass filter that is disposed in a path of the sixth light and that passes the sixth light.

[Item 12] In the biological information detection device according to Item 9, the image capturing device may further include an image sensor having an imaging surface on which the first photodetector cells and the second photodetector cells are disposed, the image sensor including first bandpass filters that face the respective first photodetector cells and that pass the second light, and second bandpass filters that face the respective second photodetector cells and that pass the sixth light, and an optical system that, in operation, forms the first image and the second image on the imaging surface.

[Item 13] In the biological information detection device according to Item 9, the image capturing device may further include an image sensor having an imaging surface on which the first photodetector cells, the second photodetector cells, and third photodetector cells are disposed, the image sensor including first bandpass filters that face the respective first photodetector cells and that pass the second light, second bandpass filters that face the respective second photodetector cells and that pass the sixth light, and third bandpass filters that face the respective third photodetector cells and that pass visible light, and an optical system that, in operation, forms the first image and the second image on the imaging surface, wherein:

the third bandpass filters may include color filters having different transmitting wavelength ranges, and the image sensor may, in operation, generate and output a color image signal by using the third photodetector cells.

[Item 14] In the biological information detection device according to any one of Items 9 to 13, the one or more arithmetic circuits may, in operation, calculate information representing blood oxygen saturation of the living body by using the first image signal and the second image signal.

[Item 15] In the biological information detection device according to any one of Items 9 to 13, the one or more arithmetic circuits may, in operation, calculate blood flow of the living body and blood oxygen saturation of the living body by using the first image signal and the second image signal, and generate information representing at least one state selected from the group consisting of a physical condition of the living body, an emotion of the living body, and a degree of concentration of the living body by using the blood flow of the living body and the blood oxygen saturation of the living body.

[Item 16] In the biological information detection device according to any one of Items 9 to 13, in a case where the first image and the second image include at least one target portion selected from the group consisting of a forehead of the living body and a nose of the living body, the one or more arithmetic circuits may, in operation, calculate a temporal change in blood flow and a temporal change in blood oxygen saturation at the at least one target portion by using the first image signal and the second image signal, and generate information representing at least one state selected from the group consisting of a physical condition of the living body, an emotion of the living body, and a degree of concentration of the living body by using the temporal change in blood flow and the temporal change in blood oxygen saturation.

[Item 17] In the biological information detection device according to any one of Items 9 to 13, in a case where the first image and the second image include a forehead and a nose of the living body, the one or more arithmetic circuits may, in operation, calculate a temporal change in blood flow and a temporal change in blood oxygen saturation at the forehead and a temporal change in blood flow and a temporal change in blood oxygen saturation at the nose by using the first image signal and the second image signal, and generate information representing at least one state selected from the group consisting of a physical condition of the living body, an emotion of the living body, and a degree of concentration of the living body, based on a first comparison between the temporal change in blood flow at the forehead and the temporal change in blood flow at the nose and based on a second comparison between the temporal change in blood oxygen saturation at the forehead and the temporal change in blood oxygen saturation at the nose.

[Item 18] In the biological information detection device according to any one of Items 1 to 17, the first light source may be a laser light source.

[Item 19] In the biological information detection device according to any one of Items 1 to 18, the image capturing device may further include an image sensor having an imaging surface on which the first photodetector cells are disposed, an optical system that, in operation, forms the first image on the imaging surface, and an adjusting mechanism that, in operation, adjusts focus of the optical system to maximize contrast of the first image.

[Item 20] In the biological information detection device according to any one of Items 1 to 19, the one or more arithmetic circuits may, in operation, determine whether the first image includes at least one target portion selected from the group consisting of a forehead, a nose, a mouth, an eyebrow, and hair of the living body by using the first image signal, and calculate the biological information of the living body in response to the first arithmetic circuit determining that the first image includes the at least one target portion.

[Item 21] In the biological information detection device according to any one of Items 1 to 20, the one or more arithmetic circuits may, in operation, further calculate different biological information of the living body by using image signal of a second portion of the first image, the second portion being different from the first portion.

[Item 22] In the biological information detection device according to any one of Items 1 to 20, the one or more arithmetic circuits may, in operation, further compare a position of the first portion in the first image at a first time point with a position of the first portion in the first image at a second time point and may, in operation, determine whether the living body has moved.

In the present disclosure, all or a part of any of a circuit, a unit, a device, a member, or a portion; or all or a part of functional blocks in the block diagrams may be implemented as one or more of electronic circuits including, but not limited to, a semiconductor device, a semiconductor integrated circuit (IC), or a large scale integration (LSI). The LSI or IC can be integrated into one chip, or also can be a combination of a plurality of chips. For example, functional blocks other than a memory may be integrated into one chip. The name used here is LSI or IC, but it may also be called system LSI, very large scale integration (VLSI), or ultra large scale integration (ULSI) depending on the degree of integration. A field programmable gate array (FPGA) that can be programmed after manufacturing an LSI or a reconfigurable logic device that allows reconfiguration of the connection or setup of circuit cells inside the LSI can be used for the same purpose.

Further, it is also possible that all or a part of the functions or operations of the circuit, the unit, the device, the member, or the portion are implemented by software-based processing. In such a case, the software is recorded on one or more non-transitory recording media such as a read-only memory (ROM), an optical disc, or a hard disk drive, and when the software is executed by a processor, the software causes the processor together with peripheral devices to execute the functions specified in the software. A system or a device may include such one or more non-transitory recording media on which the software is stored and a processor together with necessary hardware devices such as an interface.

Embodiments of the present disclosure will be described in more detail below. The following embodiments relate mainly to a biological information detection device that measures biological information in a non-contact manner, assuming that a face of a person is a living-body surface. Note that techniques of the embodiments of the present disclosure are applicable not only to a face of a person but also to portions other than the face of a person or to skin of animals other than the human.

First Embodiment

A system in which a technique of embodiments of the present disclosure is applied to non-contact heartbeat measurement will be described as a first embodiment. With a growing interest in healthcare, importance of constant biological information sensing is increasing. A system capable of constantly obtaining biological information in a non-contact manner through measurement is essential not only at hospitals but also for health management in daily life. The system according to the first embodiment is capable of monitoring heartbeat and a change in heart rate in a non-contact manner.

FIG. 2 is a diagram illustrating a schematic configuration of a living body detection system according to the first embodiment. As illustrated in FIG. 2, the living body detection system according to the first embodiment includes a light source 1, an image capturing device 2, and a computer 20. The light source 1 is located at a position apart from a living body 3 and emits a light beam of a near-infrared wavelength range. The image capturing device 2 is a camera capable of recording images of a living-body surface 4 illuminated with light. The computer 20 is connected to the light source 1 and the image capturing device 2. The computer 20 is capable of separating and measuring a component relating to surface reflected light L1 reflected from the living-body surface 4 and a component relating to inside-body scattered light L2 from a captured image. The computer 20 is capable of detecting whether an image includes a region corresponding to a living body on the basis of intensity of the surface reflected light L1 and intensity of the inside-body scattered light L2. The computer 20 is also capable of calculating and outputting biological information, such as heart rate, from a signal in a region of the image corresponding to a living body.

The light source 1 is designed to project a dot pattern onto the living-body surface 4. Typically, a dot pattern is a collection of two-dimensionally arranged small bright spots. A dot pattern of one-dimensionally arranged bright spots may be used depending on the application. In the first embodiment, for example, a random dot pattern laser projector RPP017ES available from Osela Inc. in Canada is usable as the light source 1. This laser light source emits a near-infrared laser beam of 830 nm and projects a laser dot pattern including 57446 spots in a 45°×45° viewing angle.

Figure 3A:
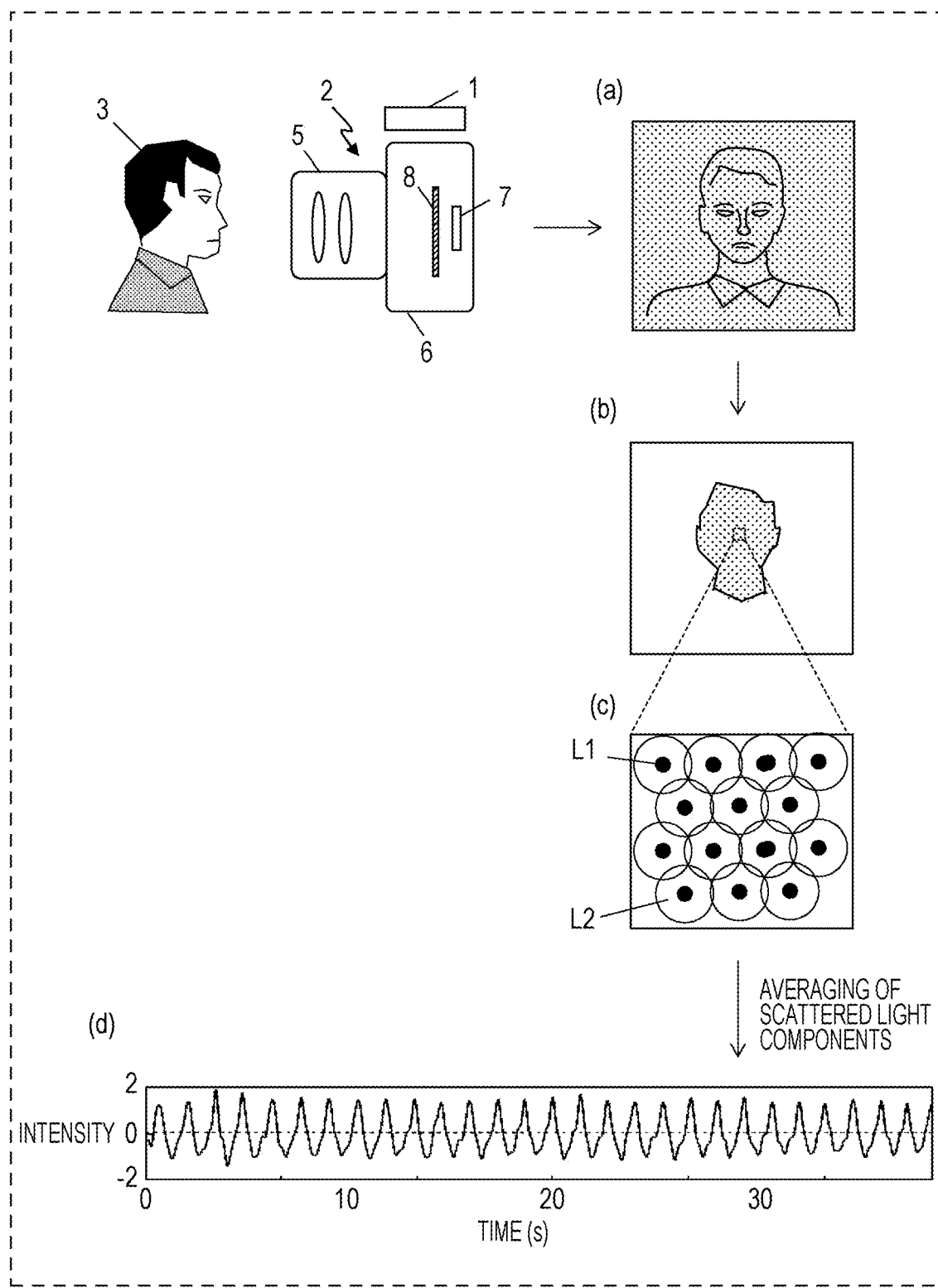
FIG. 3A is a diagram illustrating an example of a configuration of the image capturing device and examples of an image and biological information that are output in accordance with the first embodiment.

FIG. 3A is a diagram illustrating an example of a configuration of the image capturing device 2 and examples of a generated image and biological information. The image capturing device 2, which is a camera, includes an optical system 5 and a camera casing 6. The optical system 5 may be a set of a plurality of lenses. The camera casing 6 includes an image sensor 7 and a bandpass filter 8. The bandpass filter 8 passes only light having a wavelength of 830 nm±10 nm, which is the wavelength of light emitted from the light source 1.

In the case where the subject is a person, the image sensor 7 obtains a signal of an image including a plurality of points each having a brightness corresponding to an infrared reflectance at a corresponding position. Part (a) of FIG. 3A illustrates an example of an image represented by such an image signal. A arithmetic circuit of the computer 20 detects, through signal processing, only a region corresponding to a human body as illustrated in part (b) of FIG. 3A. This detection is performed based on a ratio between a signal component relating to the surface reflected light L1 and a signal component relating to the inside-body scattered light L2.

As described before, a living body has a specific optical property called "optical tissue window" for a wavelength range of red to near-infrared light. Since human skin has a small absorption coefficient and a large scattering coefficient in this wavelength range, light that has transmitted through the skin surface, which is the living-body surface 4, repeats multiple scattering and scatters inside the body and then exits from a wide area of the living-body surface 4. Accordingly, as illustrated in part (c) of FIG. 3A as an enlarged view, regions based on the inside-body scattered light L2 are present around the respective bright spots based on the surface reflected light L1 in the region corresponding to the human body in the image. The living body characteristically has a high proportion of scattered light relative to surface reflected light in the above wavelength range. In contrast, objects other than the living body have a very high proportion of surface reflected light relative to scattered light. Accordingly, a region corresponding to a living body can be detected based on the ratio between directly reflected light and scattered light. Further, biological information is successfully obtained fast by using signals of a plurality of pixels included in the living body region of the obtained image. Human body region detection based on the optical characteristics of the skin according to the first embodiment is fast and highly accurate, compared with image-recognition-based methods of the related art. Detection of a human body region and highly accurate human detection performed using the resulting information implement fast and highly accurate biological information sensing.

Figure 3B:
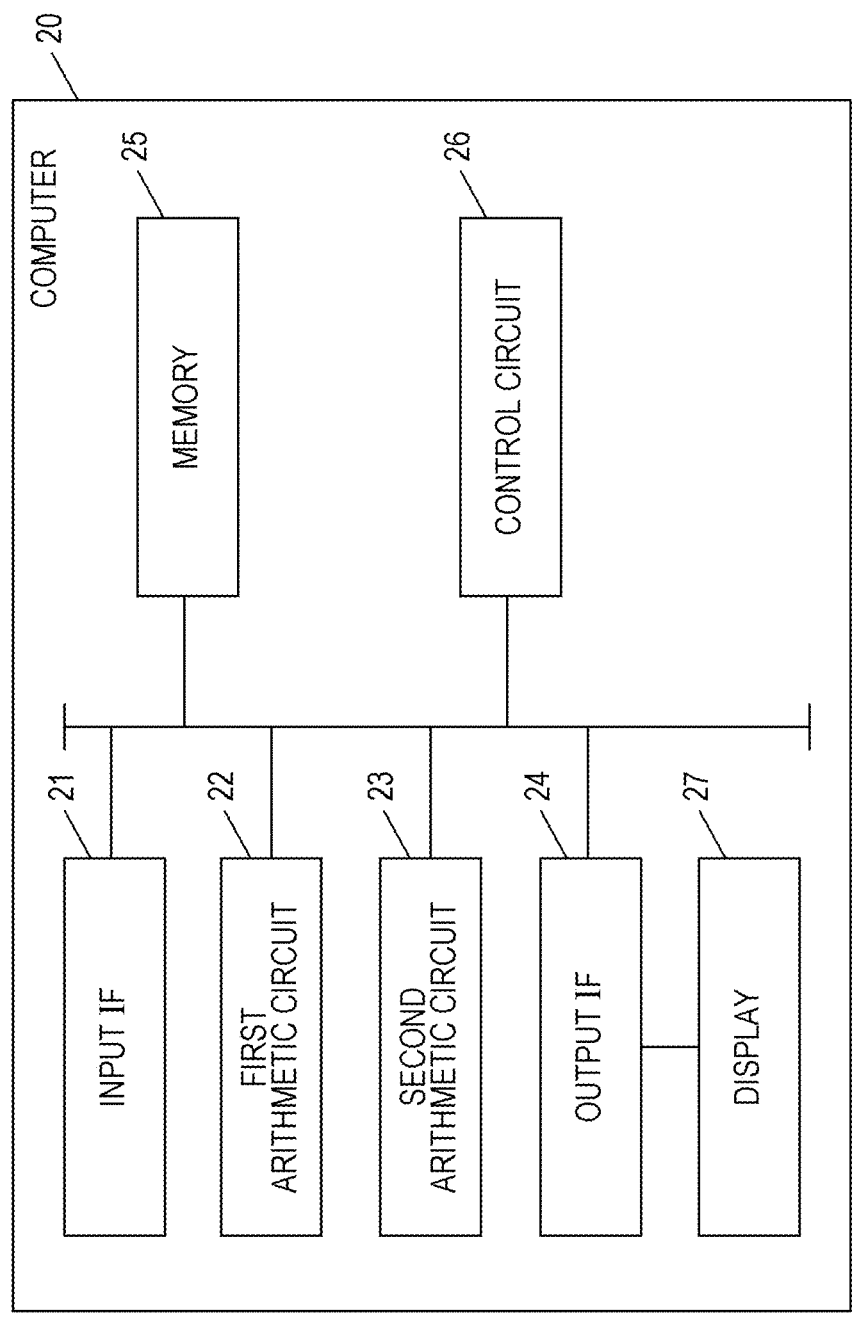
FIG. 3B is a block diagram illustrating a configuration of a computer in accordance with the first embodiment.

FIG. 3B is a block diagram illustrating a configuration of the computer 20. The computer 20 includes an input interface (IF) 21, a first arithmetic circuit 22, a second arithmetic circuit 23, a memory 25, a control circuit 26, an output interface (IF) 24, and a display 27. The input IF 21 is electrically connected to the image capturing device 2. The first arithmetic circuit 22 performs signal processing for detecting a region corresponding to a living body in an image. The second arithmetic circuit 23 calculates biological information (pulses in the first embodiment) by using image data of the detected human body region. The memory 25 stores various kinds of data. The control circuit 26 controls operations of the entire device. The output IF 24 outputs data generated by the second arithmetic circuit 23. The display 27 displays a processing result. The first arithmetic circuit 22 and the second arithmetic circuit 23 may each be an image processing circuit, for example, a digital signal processor (DSP). FIG. 3B illustrates the first arithmetic circuit 22 and the second arithmetic circuit 23 as different blocks; however, they may be implemented as a single circuit. The control circuit 26 may be an integrated circuit, for example, a central processing unit (CPU) or a microcomputer. The control circuit 26 runs a control program stored, for example, in the memory 25 to perform control, such as providing an instruction to switch on to the light source 1, an instruction to capture an image to the image capturing device 2, and an instruction to perform computation to the first arithmetic circuit 22 and the second arithmetic circuit 23. The control circuit 26, the first arithmetic circuit 22, and the second arithmetic circuit 23 may be implemented as a single integrated circuit. In the example illustrated in FIG. 3B, the computer 20 includes the display 27; however, the display 27 may be an external device electrically connected to the computer 20 wirelessly or by a cable. The computer 20 may obtain, via a communication circuit (not illustrated), image information from the image capturing device 2 located at a remote place.

In the example illustrated in FIG. 3A, the second arithmetic circuit 23 averages signal components based on the inside-body scattered light L2 of the human body region detected by the first arithmetic circuit 22. Averaging is performed for each frame of a moving image, for example. Consequently, data representing a temporal change in the average of the signal components based on the inside-body scattered light L2 is obtained as illustrated in part (d) of FIG. 3A. Heart rate (the number of heartbeats per unit time) can be determined by determining a period or a frequency from this data.

Figure 3C:
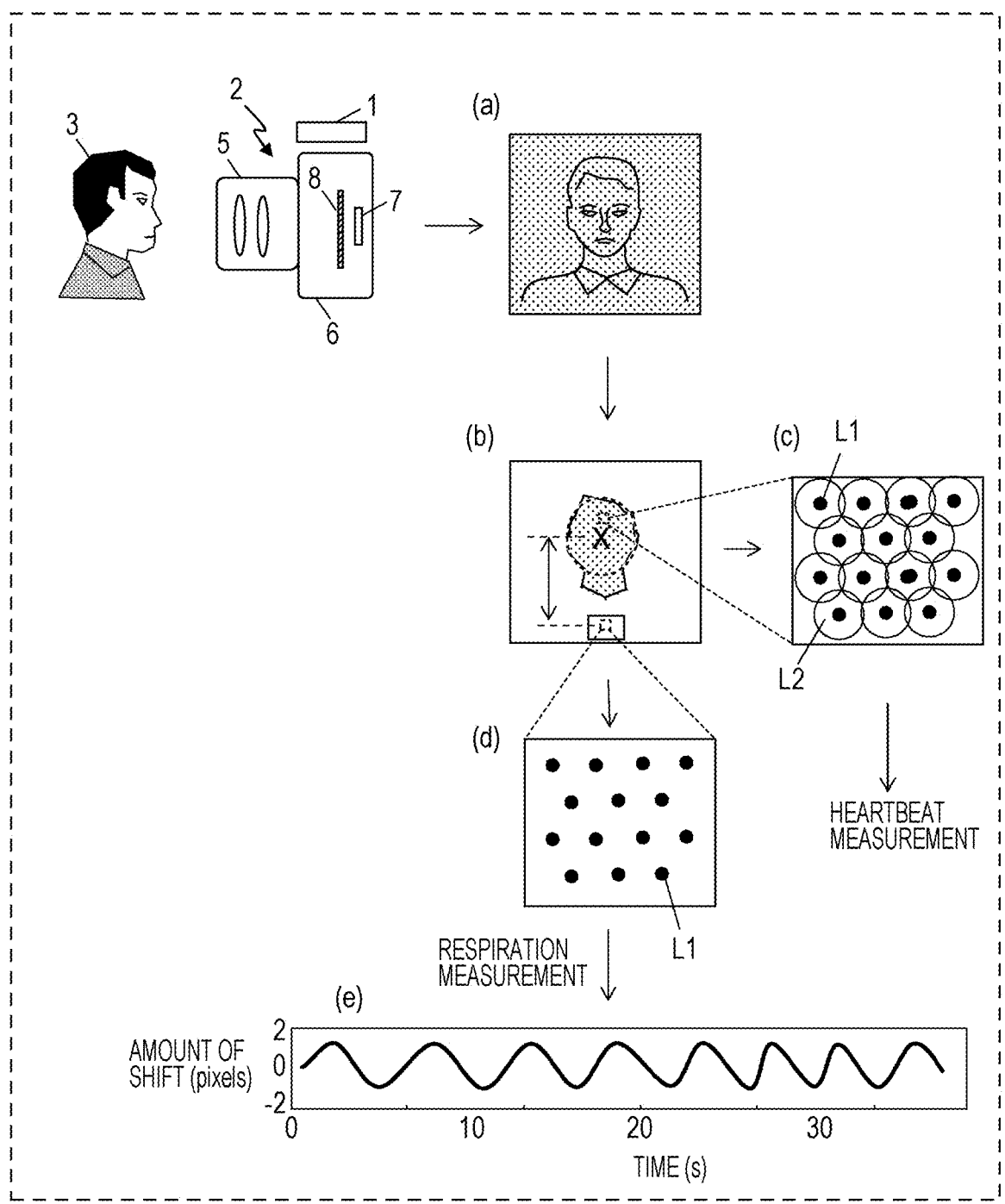
FIG. 3C is a diagram for explaining a respiration sensing method in accordance with the first embodiment.

Further, respiration measurement is also carried out simultaneously with heart rate measurement by using the similar system configuration. FIG. 3C is a diagram schematically illustrating such a system that performs respiration sensing. The hardware of this example is the same as that illustrated in FIG. 3A. With this configuration, non-contact respiration monitoring can be implemented through image signal processing.

The human respiratory interval is about 3 to 4 seconds (15 to 20 times/minute), and the chest portion and the abdominal wall expand and contract due to respiration by about 5 mm in the case of adults. If this motion of the chest portion is successfully measured with an image capturing device, respiration is successfully monitored.

A method for monitoring respiration on the basis of an amount of shift of the chest portion by using a near-infrared dot array light source is disclosed in, for example, Aoki and two others, "Non-contact and Unrestrained Respiration Watch System for Sleeping Person Using Near-infrared Bright Spots Matrix Irradiation", IEEJ Transactions on Electrical and Electronic Engineering, C. Electronics, Information and Systems, Jun. 1, 2004, Vol. 124(6), pp. 1251-1258 (hereinafter, referred to as NPL 1). The system described in NPL 1 implements highly accurate non-contact respiration sensing by determining an examination-target region for a stationary subject in advance. The system described in NPL 1 assumes non-contact respiration monitoring during sleep, and only respiration is monitored by using a large system.

In contrast, the use of the system according to the first embodiment illustrated in FIG. 3C enables respiration sensing to be performed simultaneously with heart rate sensing by using a small and inexpensive device. Further, the use of the system according to the first embodiment illustrated in FIG. 3C enables stable measurement in accordance with a body motion of the subject.

Referring to FIG. 3C, a respiration measurement method according to the first embodiment will be described below. The first arithmetic circuit 22 performs human body detection on a near-infrared image (part (a) of FIG. 3C) obtained by the image sensor 7 by using the above-described method and estimates a face region from data of the human body region (part (b) of FIG. 3C). The first arithmetic circuit 22 further estimates the position of the chest on the basis of the center of the face region. For example, a position that is shifted below from the center of the face region by a distance that is 1 to 1.2 times as large as the vertical length of the face region is estimated to be a chest region. Then, a temporal change in the position of the dot array in this chest region (part (d) of FIG. 3C) is measured. At that time, a variation in the position less than the pixel pitch can be measured by averaging variations in position of a plurality of dots. Note that positions of the dots in the captured image barely change in response to lateral-direction motion of the target (chest) and that the positions of the dots change only in response to depth-direction motion of the target and such a change is measured. In methods using an ordinary image, both lateral-direction motion of the target and depth-direction motion of the target are detected as movement on pixels. Since lateral-direction motion is detected more sensitively, measurement accuracy is low. In contrast, in the first embodiment, lateral-direction motion of the target is no longer detected and only depth-direction motion of the target is detected with the use of the dot array light source. Accordingly, highly accurate respiration monitoring can be performed. An amount of shift in the position of the dot array pattern in the chest region between frames can be determined by calculating an autocorrelation of the dot array pattern. This average shift amount represents up-down motion of the chest due to respiration. By plotting the average shift amount of the dot array pattern with respect to the time axis as illustrated in part (e) of FIG. 3C, monitoring of respiration can be performed. With the configuration of the first embodiment, highly accurate respiration sensing can be performed while tracking the chest region even if there is a body motion.

In the example illustrated in FIG. 3C, a method for measuring heart rate by using data of pixels in a forehead region of images is the same as the method illustrated in FIG. 3A. In the example of FIG. 3C, both heart rate and respiration are measured; however, respiration alone may be measured.

An example of the living body detection method that is carried out by using actual data will be described below.

Figure 4A:
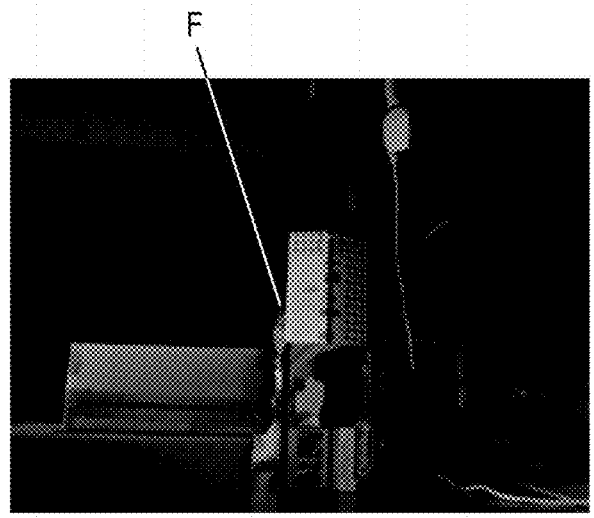
FIG. 4A is a first diagram illustrating an example of a human body detection experiment in accordance with the first embodiment.
Figure 4B:
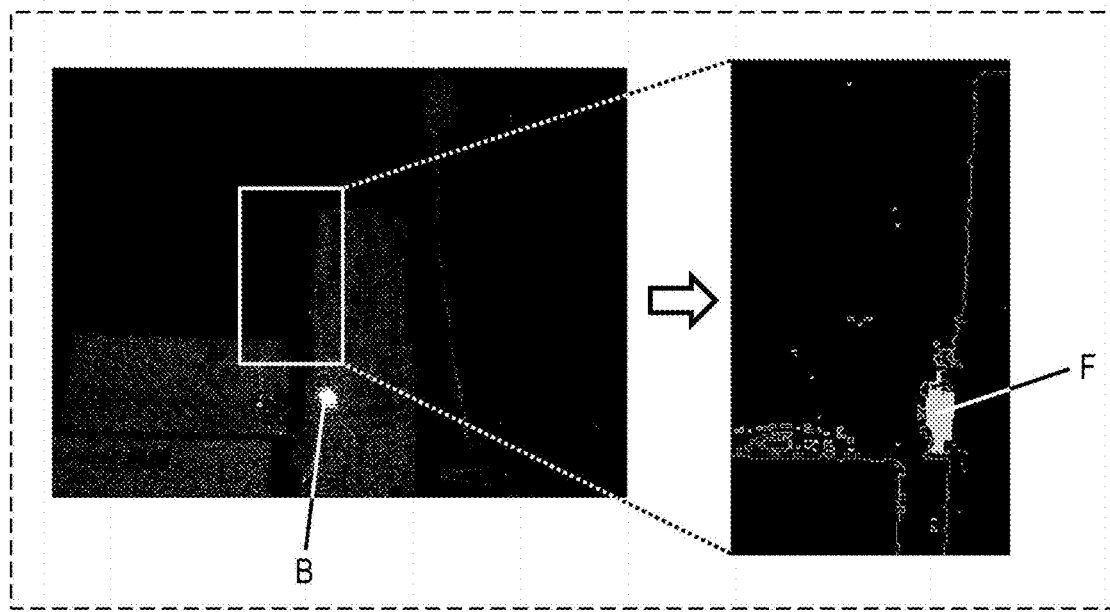
FIG. 4B is a second diagram illustrating the example of the human body detection experiment in accordance with the first embodiment.

FIG. 4A illustrates an example of an image obtained by an ordinary image capturing device that detects visible light. The central part shows a face F of a person. A left diagram in FIG. 4B shows an image of the same scene as that of FIG. 4A captured with the image capturing device 2 according to the first embodiment when the place is illuminated by the light source 1 of a wavelength of 830 nm. In this image, it is difficult to recognize the face F due to strong reflection from a box B located in the foreground. Accordingly, to detect a human body, the first arithmetic circuit 22 calculates contrast between directly reflected light and scattered light from a near-infrared image.

Figure 5:
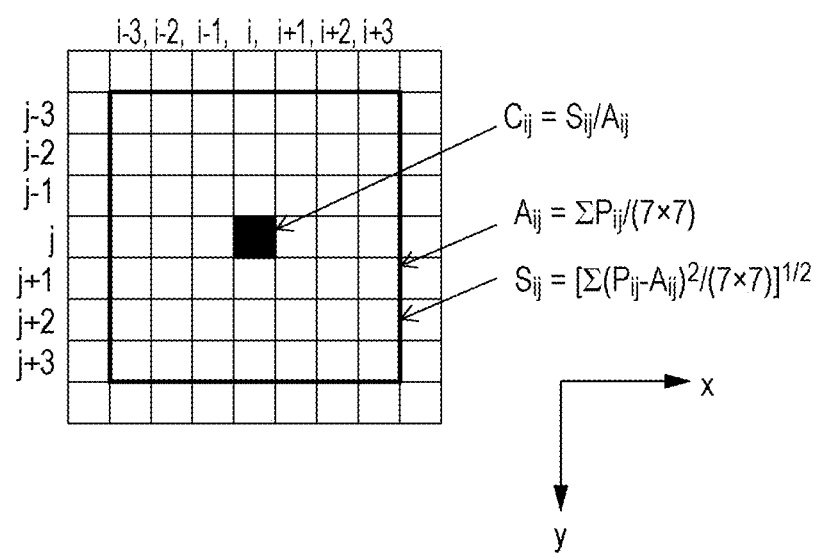
FIG. 5 is a diagram illustrating a contrast calculation method used in human body detection in accordance with the first embodiment.

FIG. 5 is a diagram illustrating an example of a pixel region used to calculate contrast. Image data is stored as two-dimensional intensity data in the memory 25. Here, Pij denotes data of a pixel located in an i-th column in the horizontal (x) direction of a j-th row in the vertical (y) direction. Contrast Cij for this pixel (i, j) is defined as follows:

$$C_{ij} = S_{ij}/A_{ij}.$$

Here, $S_{ij}$ and $A_{ij}$ respectively denote a standard deviation and an average of pieces of data of pixels in a 7×7 pixel region centered at the pixel (i, j). Since the standard deviation $S_{ij}$ decreases as the ratio of scattered light to directly reflected light increases, the value of the contrast $C_{ij}$ decreases. After repeatedly performing this processing for all pixels, the first arithmetic circuit 22 extracts only pixels for which the value of the contrast $C_{ij}$ is within a predetermined range. An example of an image that shows a part of a region where $0.2 < C_{ij} < 0.47$ is the image on the right in FIG. 4B. In this image, pixels for which the value of the contrast $C_{ij}$ is within the above range are shown in white, and the rest of the pixels are shown in black. The image indicates that a living body (i.e., the face F) is correctly extracted.

As described above, the first arithmetic circuit 22 according to the first embodiment calculates the contrast $C_{ij}$, which is a ratio between the standard deviation of pixel values of a specific pixel included in an image and a plurality of neighboring pixels of the specific pixel and the average of the pixel values of the specific pixel and the plurality of neighboring pixels. Based on the value of the contrast $C_{ij}$, the first arithmetic circuit 22 is able to determine whether a living body is located at a position corresponding to the specific pixel and output information indicating the presence or absence of the living body.

According to the first embodiment, a living body hidden behind many objects can be efficiently detected by utilizing an optical property specific to a living body. The average and the standard deviation are derived for a 7×7 pixel region to derive contrast of the image (i.e., contrast of directly reflected light and scattered light) in this example; however, this size of the pixel region is merely an example. The size (i.e., the number of pixels) of the pixel region used to compute the contrast is appropriately set in accordance with the density of a plurality of points formed by the light source 1 and the resolution of the image capturing device 2. To suppress a variance in the calculation result, a plurality of (e.g., three or more) points may be included in a pixel region subjected to computation. The accuracy of the calculated contrast value improves by increasing the number of pixels included in the region subjected to computation; however, the resolution of the resulting image of the living body decreases. Accordingly, the number of pixels included in the region subjected to computation is appropriately set in accordance with the configuration and usage of the system. Further, not only the number of pixels subjected to computation but also a pixel interval at which this processing is repeated also affect the processing speed. In the above-described processing, computation is sequentially repeated for all the pixels; however, the processing speed can be increased by increasing the pixel interval subjected to computation although the resolution decreases. This pixel interval can also be appropriately set in accordance with the configuration and usage of the system. Likewise, the predetermined contrast range is not limited to $0.2 < C_{ij} < 0.47$ and may be appropriately set in accordance with the configuration and usage of the system.

The first arithmetic circuit 22 detects, from a two-dimensional image captured by the image capturing device 2, a region of the image corresponding to a human body by using the above method. The second arithmetic circuit 23 then obtains biological information. Since the human body region is determined in the image by the first arithmetic circuit 22, biological information is generated by using pixel data of this region. The second arithmetic circuit 23 generates, as biological information, data of temporal changes in heart rate and respiration as illustrated in FIG. 3C, for example. In this way, heart rate and a change in heartbeat can be monitored in a non-contact manner.

In biological information sensing systems using a camera according to the related art, a method for detecting biological information by averaging pieces of pixel data of a living body region of an image is commonly used. In contrast, since the biological information sensing system according to the first embodiment uses a dot array light source, an unnecessary surface reflected light component reflected from the skin surface can be removed from a two-dimensional image, and inside-body scattered light containing biological information can be selectively extracted. Images (surface reflected light) of a projected dot array are detected as spots having large pixel values, and a component relating to scattering that occurs inside the body (inside-body scattered light) is detected as regions that are located around the respective dots and have a smaller pixel value than the corresponding dots. Thus, by setting a threshold for light intensity and averaging pieces of pixel data obtained by removing pieces of pixel data of a predetermined light intensity or higher, inside-body scattered light can be efficiently extracted. Through such processing, highly accurate biological information can be obtained.

Figure 6:
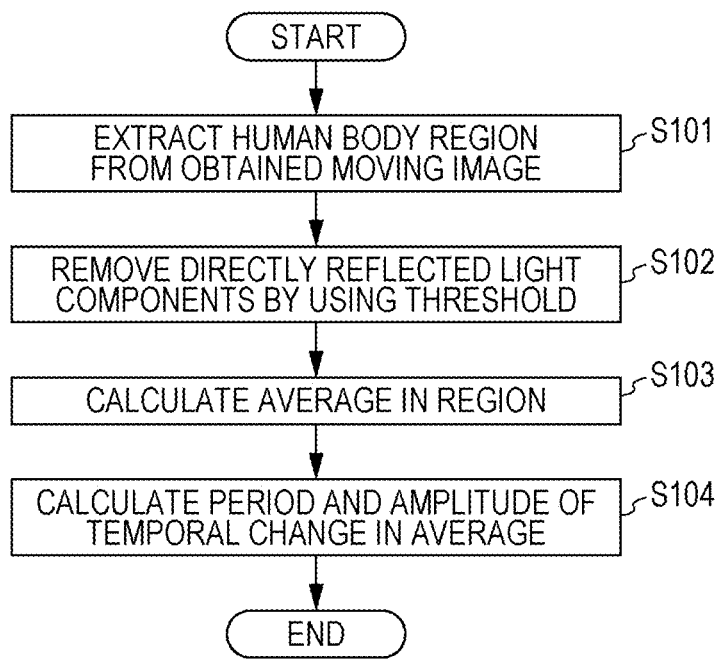
FIG. 6 is a flowchart illustrating a flow of an image processing process in accordance with the first embodiment.

FIG. 6 is a flowchart illustrating an example of an operation performed by the first arithmetic circuit 22 and the second arithmetic circuit 23 according to the first embodiment. The operations of the first arithmetic circuit 22 and the second arithmetic circuit 23 will be described by using the case where a moving image is obtained by the image sensor 7 as an example. The operation described below can be implemented as a result of one or a plurality of processors executing a computer program stored in a memory.

First, the first arithmetic circuit 22 extracts a region corresponding to a human body from the captured moving image (step S101). A method for extracting a human body region is as described above. Then, the second arithmetic circuit 23 removes pieces of data for the central portions of the dot array, which correspond to directly reflected light components, from pieces of pixel value data of the extracted human body region by using a threshold set in advance (step S102). Then, the second arithmetic circuit 23 calculates an average of the pixel values (corresponding to inside-body scattered light components) of the human body region (step S103). Steps S101 to S103 described above are performed for each frame of the moving image. The second arithmetic circuit 23 calculates a period and an amplitude of a temporal change in the average by using pieces of data of frames of a predetermined period (e.g., several to several tens of seconds) (step S104). In this way, information relating to blood flow in the body can be obtained. Since arterial blood pumped out from the heart moves along the blood vessels with fluctuation called pulses, the near-infrared absorptance and reflectance change in accordance with the pulse. Heart rate can be determined from a period of this fluctuation in the reflectance. Further, blood pressure and blood flow can be estimated from the amplitude of the pulse.

In the step of removing the directly reflected light components by using a threshold set in advance (step S102), a constant threshold can be used in the case where a distance between the image capturing device and the subject is fixed. However, since the distance between the image capturing device and the subject often varies, it is usually desirable that such a case be successfully coped with. Accordingly, for example, an average of pixel values of the entire living body region subjected to computation may be calculated, and the threshold may be changed in accordance with the average. In such an embodiment, as the average of pixel values becomes larger, the threshold can be set to be larger.

According to the first embodiment, for example, heart rate data illustrated in part (d) of FIG. 3A can be obtained. Many methods for monitoring heartbeat by using an ordinary visible-light camera and a near-infrared camera in a non-contact manner have been proposed. Since separation of surface reflected light components and scattered light components is insufficient in these methods of the related art, non-contact measurement is easily affected by disturbance light and it is difficult to implement stable and highly accurate measurement. In contrast, in the first embodiment, stable and highly accurate heartbeat measurement can be performed by spatially separating surface reflected light components and scattered light components that are contained in an obtained image signal. For example, in remote heartbeat measurement using a camera according to the related art, detection becomes unstable due to a body motion in response to vocalization during a conversation, making it difficult to perform highly accurate heartbeat measurement. However, the use of the method according to the first embodiment enables stable heartbeat measurement even when there is a body motion for a conversation.

According to the first embodiment, psychological stress of the subject can be estimated. It is known that psychological stress can be estimated from a temporal fluctuation in heart rate. When the autonomic nervous system is functioning properly, the interval between heartbeats fluctuates. It is known that the fluctuation in the interval between heartbeats decreases due to stress. The second arithmetic circuit 23 according to the first embodiment is also capable of detecting whether the subject has psychological stress and detecting the degree of psychological stress on the basis of the change in the fluctuation in the interval between heartbeats. To constantly perform stress sensing in daily life, an unconstrained and non-contact heartbeat sensing technology such as the first embodiment is important.

As described above, the use of the system according to the first embodiment makes it possible to monitor heart rate or blood pressure all the time including a sleeping period without constraining the subject. Consequently, for example, a system can be constructed that constantly monitors the condition of the patient at hospitals and alerts medical personnel when anything unusual occurs. In addition, for example, monitoring of heart rate of a patient who has sleep apnea syndrome can be performed at nighttime at home. Further, since stress sensing can be easily performed in daily life as described above, people can enjoy their daily life more.

Second Embodiment

In the first embodiment, the system that detects a human body region from an image and obtains biological information from the human body region of the image has been described. Typical application examples that use human body detection will be described below as a second embodiment. Development relating to human body detection is underway for the purpose of detecting disaster victims buried under rubble or the like at a disaster site, for example. Finding disaster victims within 72 hours from occurrence of a disaster is critical in terms of the survival rate of disaster victims. Accordingly, a simple and stable living body detection system is needed. The living body detection technology is also utilized in fields of security and transportation. The living body detection technology plays an important role to find an intruder in the field of security and to detect foot passengers in the field of transportation. There is also an increasing need for a system capable of selectively detecting a living body (especially, person) in an image including various constructions or objects. A living body can be detected by the operation of the first arithmetic circuit 22 according to the first embodiment. However, more accurate and more reliable living body detection can be implemented by further performing sensing of biological information (e.g., presence or absence of pulses) on a region where a living body is detected. Operations according to the second embodiment will be described below for each application.

The physical configuration of the second embodiment is substantially the same as that of the first embodiment.

(1) To Find Disaster Victims at Time of Disaster

Quickly finding disaster victims buried in rubble in response to occurrence of a natural disaster, such as earthquake, tsunami, or debris flow, is particularly important to save people's lives. There is "golden time of 72 hours", which indicates that the survival rate greatly decreases after 3 days, and it is necessary to quickly find disaster victims in a chaos circumstance. The use of the system according to the second embodiment makes it possible to detect disaster victims hidden behind rubble in real time by capturing an image even in a circumstance where rubble is scattered everywhere. Since the system is small, the system can be installed on an unmanned aerial vehicle (UAV), which is so-called a drone, for example. This configuration makes it possible to capture an image while remotely controlling the system at a remote location and to search for survivors even if a disaster site is difficult to access because of a risk of a secondary disaster.

Human body detection can be performed through living body detection processing performed by the first arithmetic circuit 22 according to the first embodiment. However, to improve the accuracy, the processing result obtained by the second arithmetic circuit 23 is further utilized in the second embodiment. Specifically, the second arithmetic circuit 23 performs sensing of biological information (e.g., the presence or absence of pulses) in a region (referred to as a living body region) estimated to correspond to a living body by the first arithmetic circuit 22. In this way, a human body can be detected more accurately. By determining the presence or absence of a body motion in the living body region, erroneous detection can be reduced and reliability can be increased. The presence or absence of a body motion can be determined on the basis of whether there is a temporal change in the living body region by comparing a plurality of consecutive frames, for example. Further, the living body detection accuracy can be increased drastically by determining the presence or absence of heartbeats by using pieces of pixel data of the living body region. In accordance with the second embodiment, fast and highly reliable living body detection can be performed by using living body detection based on the optical characteristics of the skin, body motion detection based shifting of the living body region, and heartbeat measurement calculated from signal intensity in the living body region in combination. Further, since the physical conditions of disaster victims can be determined from biological information, the rescue priority can be determined based on the data.

More reliable living body detection can be implemented in applications of human body detection described below by using pieces of information obtained by (1) living body detection, (2) body motion detection, and (3) heart rate detection in combination in accordance with the second embodiment.

(2) For Use in Monitoring

Surveillance cameras are widely used and contribute to safe and secure daily life of people. As the number of surveillance cameras increases, it becomes more important how and who checks a video image captured by the surveillance cameras. Since it is difficult for a person to check the image all the time, a usage is common in which the image is accumulated and the image is checked after occurrence of a problem (crime) to grasp the situation. A utilization method may be adopted in which the moment at which a problem occurs is captured from a real-time image and the problem is immediately dealt with. The use of the technique according to the second embodiment of the present disclosure makes it possible to construct a system that recognizes a person when the person enters the field of view of a surveillance camera and warns a person in charge to prompt the person in charge to check the image in real time. A system can be constructed that frees the person in charge from the necessity of standing by in front of the monitor of the surveillance camera and that displays a warning and the image on a mobile terminal carried by the person in charge upon detecting a person. Such a system is suitable for monitoring at a backdoor of a warehouse or building where people rarely appear or a place where access is restricted. In addition, for a place, such as a building, where images captured with many surveillance cameras are collectively monitored, highlighting a video image in which a certain person is detected may be useful to prevent an unusual situation from being overlooked or to find out an unusual situation at an early stage.

More important information can be obtained for the purpose of monitoring by sensing biological information (presence or absence of pulses) by using the second arithmetic circuit 23 in addition to detection of a suspicious person. The psychological nervousness can be estimated from heart rate or the fluctuation in heartbeat of a suspicious person in a monitored image. The degree of danger (alert level) of that person can be estimated from the estimated nervousness. Security systems that detect possible criminals from crowd at airports or commercial facilities by using images obtained with cameras are under development. The living body detection/living body sensing system according to the second embodiment is also applicable for such a purpose.

As for monitoring, development of a method in which a computer performs object recognition is in progress thanks to the advance in the image recognition technology, instead of a traditional method in which a person judges a monitoring image. For such a usage, a common method is that an image is transmitted to a host computer and the host computer performs recognition. However, since this method requires image data be transmitted to the host computer, this method involves issues such as an increasing amount of communications, a decreasing communication rate, and an increasing load of the host computer. If a surveillance camera is capable of performing preliminary recognition and judgement on an image, the load for communication, storage, and computation can be greatly reduced. However, if the recognition is not sufficiently reliable, the recognition may lead to overlooking of an event. Since a person can be highly reliably detected with the human body detection method according to the second embodiment, only a partial image including a person can be selectively transmitted to the host computer upon detecting the person. Consequently, the surveillance system can be efficiently operated.

In addition, the progress in the image recognition technology makes it possible to identify an individual from an image at a high accuracy. In terms of identification of an individual from an image, a method in which an image is transmitted to a host computer and the host computer performs recognition is commonly used; however, this method also involves issues relating to load for communication, storage, and computation as described above. An operation for extracting a face portion for face recognition imposes a heavy load during computation. The use of the human body detection method according to the second embodiment allows the face portion to be easily extracted from an image. Accordingly, only the part of the image for the face portion can be transmitted to the host computer for individual identification, and the load for identifying an individual can be greatly reduced. Further, if the number of people to be identified is limited, a surveillance camera is able to immediately identify an individual without using the host computer by registering characteristics of the people in the surveillance camera in advance.

(3) For Use in Vehicles

Installation of the system according to the second embodiment in a vehicle makes it possible to recognize foot passengers on the street and implement safer driving. Even when a person is hidden behind an object and is scarcely seen, the system can detect the person and warn the driver. In terms of automated driving, in a situation where a vehicle cannot stop in response to breaking and an accident is inevitable even if the vehicle changes the direction to the left and to the right, a question about which direction the vehicle should head occurs. In such a case, it is effective to detect people with the system according to the second embodiment and to change the heading direction to a direction in which the vehicle can avoid people. Since it is desired that the system quickly and highly accurately detect people in such a usage, the system according to the second embodiment is particularly suitable.

(4) Person Detection Switch

There is a wide variety of usages in which power is switched on and off by detecting a person. For example, there are usages in which switching of a device such as an air-conditioner or a light is controlled by detecting a person in a room, an automatic door is controlled at a high accuracy, a traffic light for foot passengers is controlled by detecting of a foot passenger at crossing, and brightness of an illumination of a vending machine is changed. The second embodiment is applicable to such usages. The use of the system according to the second embodiment can implement a sophisticated switch that does not respond to an object or pet but responds only to people. In such a usage, a small person detection sensor unit including the light source, the image capturing device, and the arithmetic circuit of the system according to the second embodiment may be constructed.

(5) Biometric Authentication

Biometric authentication, such as fingerprint authentication, iris authentication, and vein authentication, is widely used as a method for authenticating an individual. With the increasing use of such authentication, cases and a risk of spoofing in biometric authentication are increasing. An image duplication technology, such as copying, has been used in image-based authentication. Recently, with an increasing use of iris authentication and a three-dimensional printer, a risk of spoofing using a highly precise duplicate is increasing. As a countermeasure for such a risk, a two-step authentication system is effective. For example, a method is effective in which ordinary biometric authentication is performed after checking that a target is a living body by using the living body detection system according to the second embodiment. By checking that the target is a living body by using the living body detection system according to the second embodiment, the reliability of biometric authentication can be increased.

In the usages (1) to (4) out of the above-described usages, the second arithmetic circuit 23 may generate image data in which a region determined to be a human body is superimposed on a visible-light-based image and display the resulting image on a display. Since people have a different visual impression from a single image representing the human body region or from an image in which an infrared image and a near-infrared image representing the human body region are superimposed, there is an issue about how a person recognizes the position of a human body even when the human body is detected. To address this issue, a visible-light camera may be added to the system illustrated in FIG. 3A. The second arithmetic circuit 23 may superimpose a visible-light-based image obtained by the visible-light camera and a near-infrared image obtained by the image sensor 7 to generate image data in which the human body region is superimposed on the visible-light-based image. By displaying the human body region on the visible-light-based image in an emphasized manner, the noticeability can be increased. In usages in which a person makes a judgement after a human body is detected, a system capable of superimposing an image of the human body region on a visible-light-based image is more effective.

Further, in the case where the system additionally including a visible-light camera is used, the second arithmetic circuit 22 may extract an outline of an image from a visible-light-based image and remove a portion corresponding to the outline from a region estimated to be a human body region. This is because an outline region of an object is erroneously detected as a human body since the infrared reflectance sometimes changes greatly at the outline portion of an object. By removing the outline region, an image of a human body region containing less noise can be obtained.

In order to obtain a visible-light-based image and a near-infrared image for use in human body detection by using a single camera, a visible-light cut-off filter is removed from the camera and visible light and near-infrared light may be switched between every frame by associating illumination light with the frame rate of the camera. With such a configuration, a visible-light-based image and a near-infrared image can be obtained by using a single camera. Advantages of this method are that there is no parallax between cameras and superimposition of images is easy because a visible-light-based image and a near-infrared image can be obtained by using a single camera.

Third Embodiment

A more specific application example in which human body detection and biological information sensing are used in combination will be described as a third embodiment. As described above, the system according to embodiments of the present disclosure is capable of quickly detecting a human body and quickly and highly accurately obtaining biological information, such as heartbeats, from data of the detected human body region. By using this system, a watch system installed in personal spaces such as a bathroom, a lavatory, and a bedroom can be implemented. It is particularly important to consider the privacy in personal spaces. Systems that constantly capture images of a subject with a high-resolution camera and that use such images involves a concern about violation of privacy due to leakage of the images and imposes psychological load during image capturing due to the presence of the camera. Such issues are coped with by the watch system according to the third embodiment.

With population aging, it is said that ten thousands to twenty thousands of people die in the bathroom in Japan. This number is much larger than the number of people who die in traffic accidents, which is four to five thousands of people. The causes of death in the bathroom include accidents (death by drowning) and diseases (attacks due to cardiovascular disorders and brain disorders). Many of people who die in the bathroom are elderly people, and many people die in winter. With population aging, the annual number is also increasing. Death cases that occurred in the bathroom include many cases in which the life can be saved if an unusual situation can be detected soon after the occurrence regardless of whether the death results from an accident or a disease. Since the bathroom is a closed private space, there are many cases where late discovery results in death. A system capable of watching a target person in the bathroom while paying considerations to privacy is strongly desired.

Figure 7A:
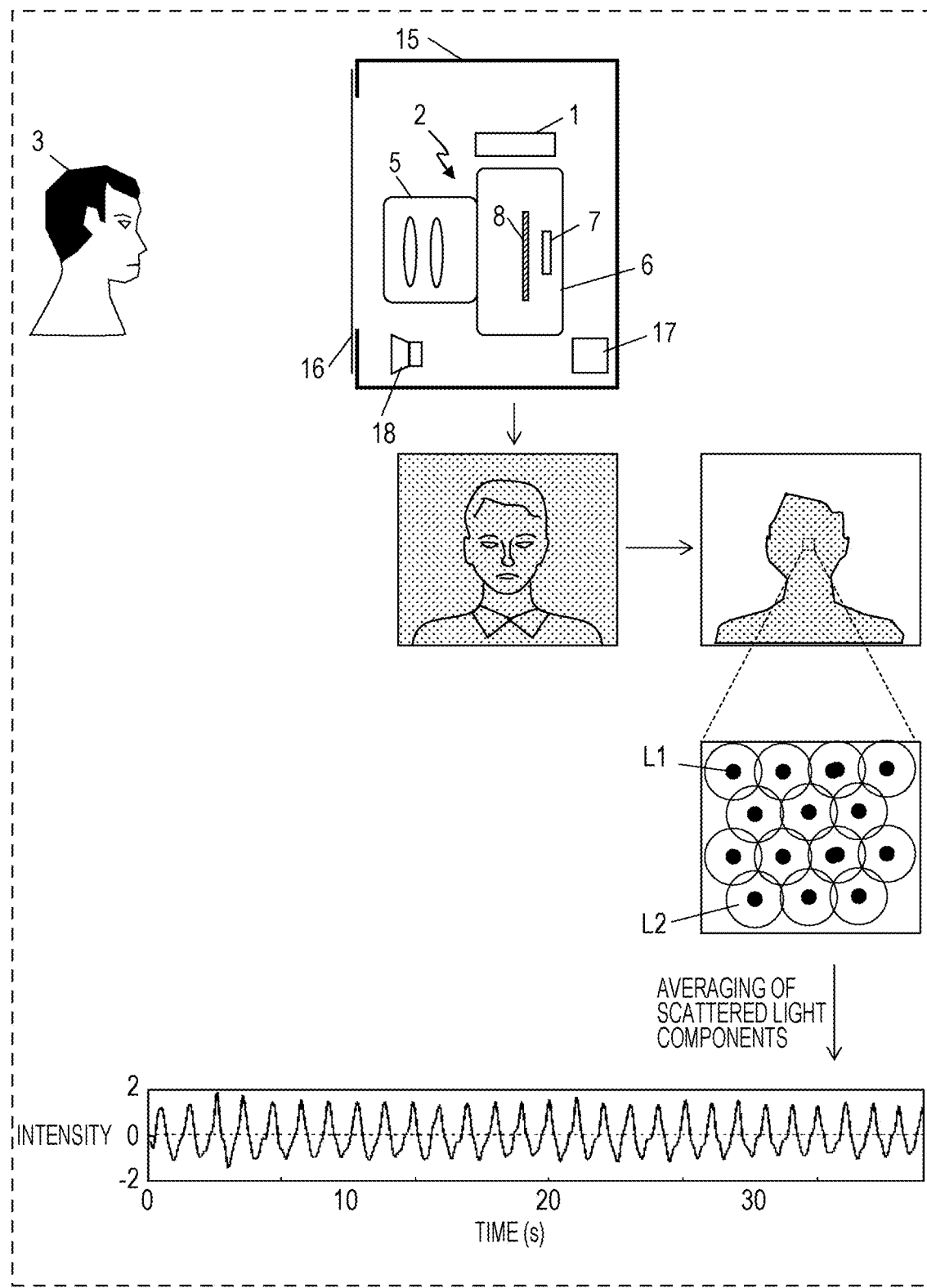
FIG. 7A is a diagram schematically illustrating a biological information detection device and a processing process of the biological information detection device in accordance with a third embodiment.

FIG. 7A is a diagram schematically illustrating a biological information detection device according to the third embodiment and a processing process performed thereby. The configuration of the biological information detection device according to the third embodiment is substantially the same as that illustrated in FIG. 3A. However, in the third embodiment, the light source 1 and the image capturing device 2, which is a camera, are housed in a casing 15 having a water-resistance function in consideration for the use in the bathroom. The casing 15 has an opening at a frontal surface thereof so as not to block light from a light source 1 and light returning from a subject 3. At the opening, a filter 16 that transmits near-infrared light is provided. Near-infrared light emitted from the light source 1 passes through the filter 16 and is incident on the subject 3. The near-infrared light reflected from the subject 3 passes through the filter 16 again, passes through an optical system 5, which includes lenses of the image capturing device 2, and a bandpass filter 8, and is incident on an image sensor 7.

The biological information detection device illustrated in FIG. 7A further includes a speaker 18 that issues an alert (alarm) and a control device 17. The control device 17 is connected to and controls the image capturing device 2, the light source 1, and the speaker 18. The control device 17 is a component equivalent to the computer 20 illustrated in FIG. 2 and includes the first arithmetic circuit 22, the second arithmetic circuit 23, the memory 25, and the control circuit 26 illustrated in FIG. 3B. The control circuit 26 of the control device 17 instructs the speaker 18 to issue an alert upon detecting anything unusual.

In the third embodiment, the system is configured to be water-proof and is configured such that the image capturing device 2 is hidden from the eyes. With such configurations, psychological burden of being imaged in the bathroom can be reduced. The basic system configuration and the signal processing are substantially the same as those of the first embodiment.

An actual watch algorithm according to the third embodiment will be described below with reference to FIGS. 7B and 7C. In the third embodiment, the biological information detection device illustrated in FIG. 7A (also referred to a "watch system") is installed at the corner of the bathroom and is configured to be able to monitor the entire bathroom as illustrated in part (a) of FIG. 7B. Human body detection (part (b) of FIG. 7B), body motion detection (part (c) of FIG. 7B), and detection of abnormal heartbeat (part (d) of FIG. 7B) are performed by using data of near-infrared images obtained by image capturing. If there is no body motion after the human body is detected, for example, a first alert (alert 1) is issued to a person who is taking a bath to draw the person's attention. Further, if abnormal heartbeat is detected, a second alert (alert 2) is issued to people located outside the bathroom, for example. The operation of the watch system according to the third embodiment will be described in more detail below with reference to a flowchart of FIG. 7C.

Figure 7C:
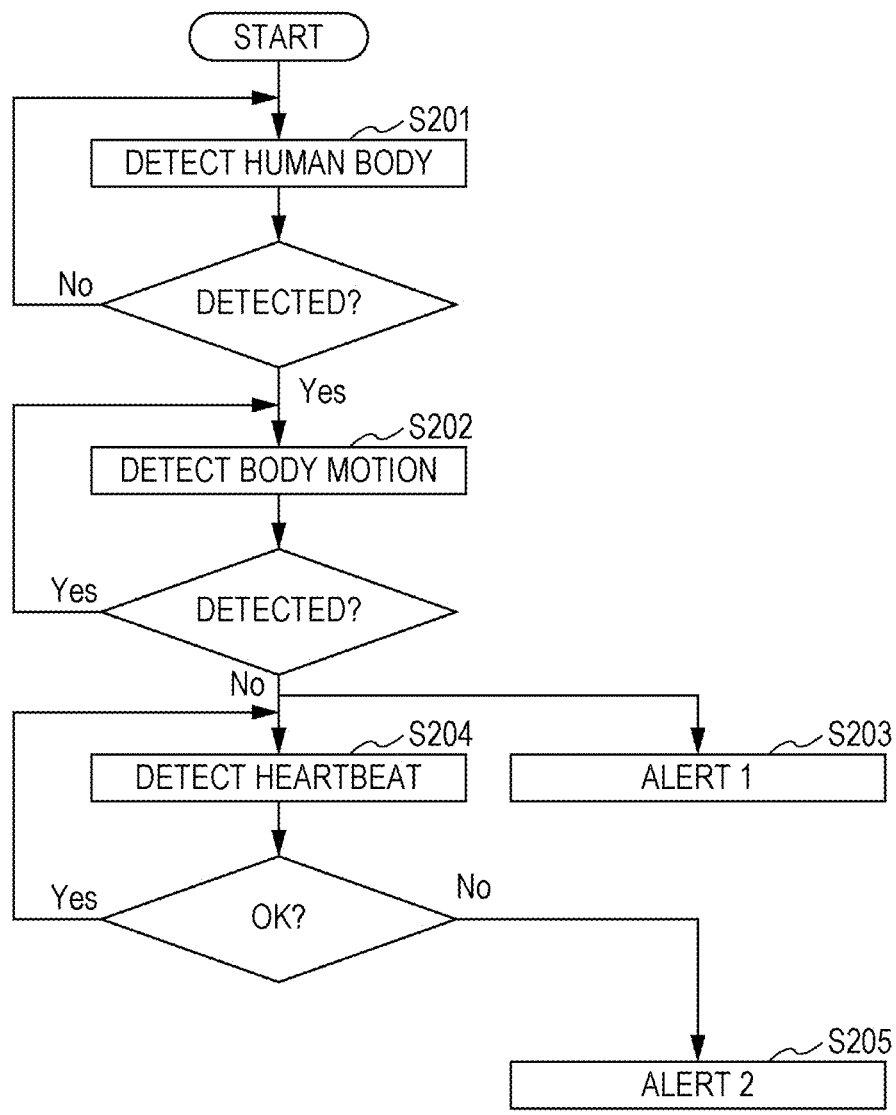
FIG. 7C is a flowchart illustrating the algorithm of the watch system in accordance with the third embodiment.

FIG. 7C is a flowchart illustrating an operation of the watch system according to the third embodiment. First, the first arithmetic circuit 22 performs human body detection by using the same method as that used in the first embodiment on the basis of data of captured near-infrared images (S201). If a human body is detected, the process proceeds to step S202 of body motion detection. At that time, data of the image used in human body detection is not stored in a storage device (e.g., the memory 25 illustrated in FIG. 3B) and is overwritten by data of the next frame image except for the data of the human body region. Since image data that allows identification of an individual is not left, privacy is protected.

Then, the second arithmetic circuit 23 detects a body motion by comparing pieces of data of the detected human body region of a plurality of consecutive frames (step S202). For example, if no body motion is detected for a predetermined period (e.g., 30 seconds) or more, the alert 1 is issued to the subject (step S203). The alert 1 can be an alert, for example, "Are you awake? It is dangerous to sleep in the bath. Please press the OK button if you are awake."The alert 1 is intended to draw the attention of the subject and to check the condition. When no body motion is detected, the second arithmetic circuit 23 measures pulses (step S204). If the pulses are slow or no pulse is detected, the alert 2 is issued (step S205). The alert 2 is an alert for people (such as a family member, a caregiver, or an ambulance crew) located outside the bathroom. The alert 2 can be an alert intended to request a target person set in advance in the system to check the situation or to request a rescue via voice alert, telephone, or the Internet.

In accordance with the third embodiment, three-step detection of (1) human body detection, (2) body motion detection, and (3) heartbeat measurement can be performed with a simple system configuration. Accordingly, highly reliable watch can be implemented.

In the above-described example, the three-step detection of (1) human body detection, (2) body movement detection, and (3) heartbeat measurement is sequentially performed step by step; however, the detection need not be performed in this order. For example, body motion detection and heartbeat measurement may be performed in parallel after human body detection. In this way, heartbeat of a person who is taking a bath can be constantly monitored and an appropriate advance can be given to the person who is taking a bath. Death from drowning often occurs because of dizziness (in the bathroom) that results from occurrence of orthostatic hypotension, which occurs in response to a change in heartbeat in response to contraction of blood vessels due to a temperature difference between a changing room and a bathroom and which occurs in response to a decrease in blood flow in the brain and the heart in response to an increase in blood flow at the body surface. A change in the physical condition of a person who is taking a bath can be detected in real time by constantly monitoring heartbeat as in the third embodiment. Upon detection of a change in the physical condition, a feedback is given to the person who is taking a bath. In this way, the above-described accident can be avoided. For example, when an increase in heat rate is large, a message such as "You need to be careful for dizziness. When you stand up, please do so slowly while holding the handrail." can be issued.

Protection of privacy is especially important in a watch system installed in private spaces, such as a bathroom, a lavatory, and a bedroom. In the third embodiment, near-infrared images obtained with a camera are used only for human body detection, and the image data is not stored in a storage medium and is constantly overwritten by data of the next frame after the human body detection processing. In addition, the system according to the third embodiment is designed so as not to include an image data output mechanism. Accordingly, it is impossible to obtain image data from outside. That is, the system is configured so that privacy is not violated even when the system is attacked by a malicious hacker. In addition, since the camera can be hidden so as not to be seen from the outside by the use of near-infrared light, watch can be done without causing the subject to have a feeling of being imaged. In the watch system installed in private spaces, it is particularly essential to ensure privacy in both the hardware aspect and the psychological aspect. The third embodiment implements watch at home while considering the privacy.

Fourth Embodiment

A system for measuring blood oxygen saturation in a non-contact manner will be described as a fourth embodiment. The main role of blood is to receive oxygen at lungs, carries oxygen to tissues, receives carbon dioxide from tissues, and carries carbon dioxide back to lungs. Approximately 15 g of hemoglobin is present in 100 ml of blood. Hemoglobin loaded with oxygen is called oxyhemoglobin ($HbO_2$), whereas hemoglobin not loaded with oxygen is called hemoglobin or deoxyhemoglobin (Hb). As illustrated in FIG. 22, oxyhemoglobin and deoxyhemoglobin have different light absorption properties. Oxyhemoglobin absorbs infrared light having wavelengths exceeding approximately 830 nm relatively well, whereas deoxyhemoglobin absorbs red light (e.g., a wavelength of 660 nm) relatively well. There is no difference between absorbance of oxyhemoglobin and absorbance of deoxyhemoglobin for near-infrared light having a wavelength of 830 nm. Accordingly, in the fourth embodiment, transmitting light having these two wavelengths, that is, 660 nm and 830 nm, are measured. A ratio (oxygen saturation) between two types of hemoglobin can be determined from a ratio between transmitting light of infrared light and transmitting light of red light. Oxygen saturation is a value indicating how much hemoglobin in blood is loaded with oxygen. The oxygen saturation is defined by Equation below.

$$\text{Oxygen saturation} = C(HbO_2)/[(C(HbO_2)+C(Hb)] \times 100 \text{ (\%)},$$

where C(Hb) denotes a deoxyhemoglobin concentration, and $C(HbO_2)$ denotes an oxyhemoglobin concentration.

A living body includes a non-blood components that absorb light having a wavelength of red to near-infrared light; however, a temporal fluctuation in light absorbance results mainly from hemoglobin in arterial blood. Accordingly, blood oxygen saturation can be measured at a high accuracy, based on a fluctuation in absorbance. Arterial blood pumped out from the heart moves through a blood vessel as a pulse wave, whereas venous blood does not have a pulse wave. Light illuminating a living body transmits through the living body after being absorbed at each layer of the living body, such as arteries, veins, and non-blood tissues. At that time, thickness of such tissues other than arteries does not change over time. Accordingly, scattered light from the living body shows a temporal change in intensity in response to a change in thickness of an arterial blood layer due to the pulse. This change reflects a change in thickness of the arterial blood layer, and does not contain the influence of venous blood and tissues. Thus, by focusing only on the change in the scattered light component, information concerning arterial blood can be obtained. Also, heart rate can be determined by measuring a period of a change in the component over time.

FIG. 8 is a diagram illustrating a configuration of the system according to the fourth embodiment. The system includes light sources 101 and 102, image capturing devices 201 and 202, and a computer 20. The light sources 101 and 102 are two array point light sources that are disposed at positions away from a living body 3 and emit a light beam of a wavelength of near-infrared light (e.g. wavelength of 830 nm) and a light beam of a wavelength of red light (e.g. wavelength of 660 nm), respectively. The image capturing devices 201 and 202 are two cameras capable of recording an image of a living-body surface 4 illuminated with light. The computer 20 separates and measures an intensity of directly reflected light reflected from the living-body surface 4 and an intensity of scattered light caused inside the living body from the obtained image and calculates biological information from the intensity of the directly reflected light and the intensity of the scattered light. In the fourth embodiment, the system includes the light sources 101 and 102 with different wavelengths and the image capturing devices 201 and 202 respectively corresponding to the light sources 101 and 102 in order to measure blood oxygen saturation.

Figure 9:
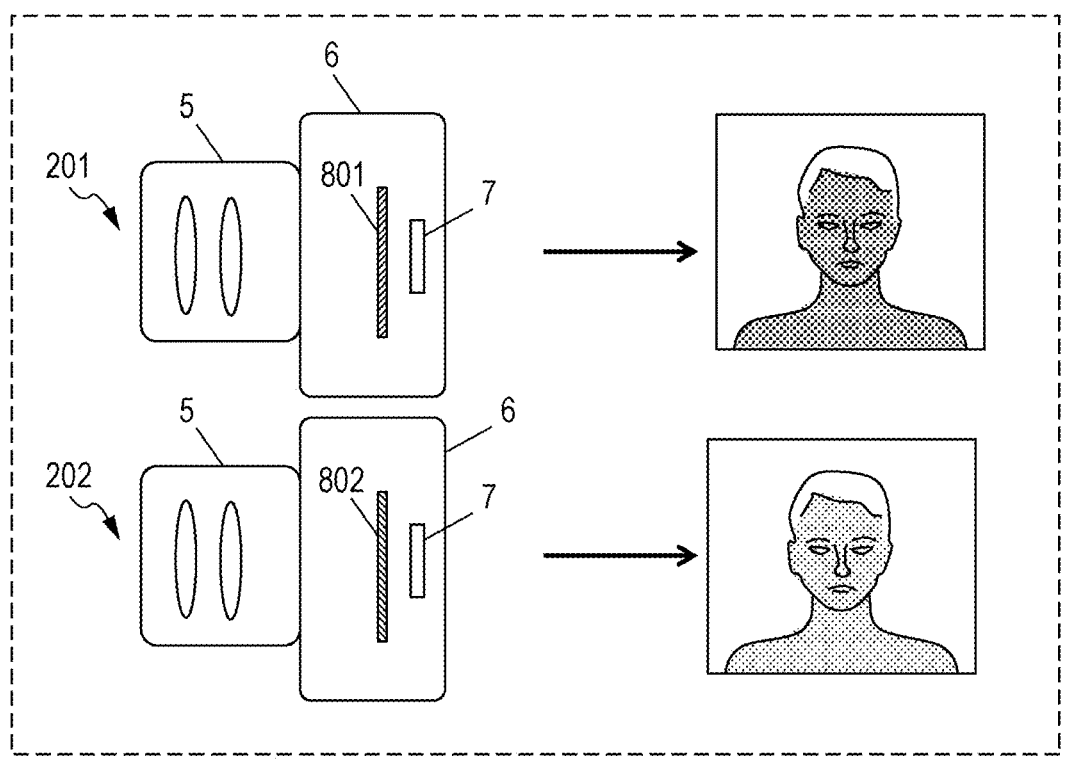
FIG. 9 is a diagram illustrating the overview of biological information sensing that uses two image capturing devices in accordance with the fourth embodiment.

FIG. 9 is a diagram illustrating a configuration of the image capturing devices 201 and 202. Each of the image capturing devices 201 and 202 includes an optical system 5, which includes lenses, and a camera casing 6. The camera casing 6 of the image capturing device 202 includes an image sensor 7 and a bandpass filter 802 that selectively passes near-infrared light (wavelength of 830 nm). The camera casing 6 of the image capturing device 201 includes the image sensor 7 and a bandpass filter 801 that selectively passes red light (wavelength of 660 nm).

For example, a random dot pattern laser projector RPP017ES available from Osela Inc. in Canada can be used as the light source 101. This laser light source is an 830-nm near-infrared laser light source and projects a laser dot pattern including 57446 spots in a 45°×45° viewing angle. For example, a random dot pattern laser projector RPP016ES available from Osela Inc. in Canada can be used as the light source 102. This laser light source is a 660-nm red laser light source and projects a laser dot pattern including 23880 spots in a 35°×35° viewing angle.

The computer 20 controls the image capturing devices 201 and 202 and the light sources 101 and 102 so that the two image capturing devices 201 and 202 operate together to simultaneously capture respective images. In this way, images based on light having two different wavelengths are generated by the image capturing devices 201 and 202 as illustrated on the right in FIG. 9, for example.

Figure 10:
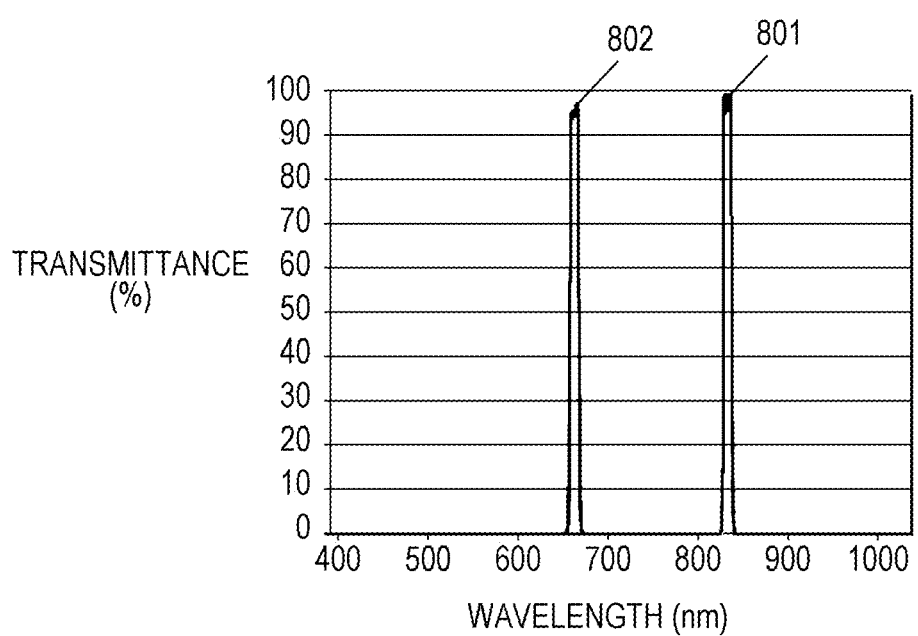
FIG. 10 is a diagram illustrating transmittance characteristics of two bandpass filters in accordance with the fourth embodiment.

FIG. 10 is a diagram illustrating transmittance characteristics of the bandpass filters 801 and 802. The bandpass filter 801 has a transmittance characteristic that the transmission center wavelength is 830 nm and the bandwidth is 10 nm. The bandpass filter 802 has a transmittance characteristic that the transmission center wavelength is 660 nm and the bandwidth is 10 nm. The transmission center wavelengths of the bandpass filters 801 and 802 respectively match central values of wavelengths of the light sources 101 and 102. Accordingly, the image capturing device 201 obtains an image based on light having a wavelength of 830 nm, whereas the image capturing device 202 obtains an image based on light having a wavelength of 660 nm.

The first arithmetic circuit 22 of the computer 20 first extracts a human body region from a moving image as in the first embodiment. The first arithmetic circuit 22 then performs data selection on pieces of data of pixels in that region by using a threshold to remove directly reflected light components. Then, the first arithmetic circuit 22 calculates an average of pixel values of the pixels in the measurement-target region. The first arithmetic circuit 22 performs the above process for each of the image capturing device 201 for 830 nm and the image capturing device 202 for 660 nm. The averages thus obtained indicate intensities of scattered reflected light from the living body 3.

Figure 11:
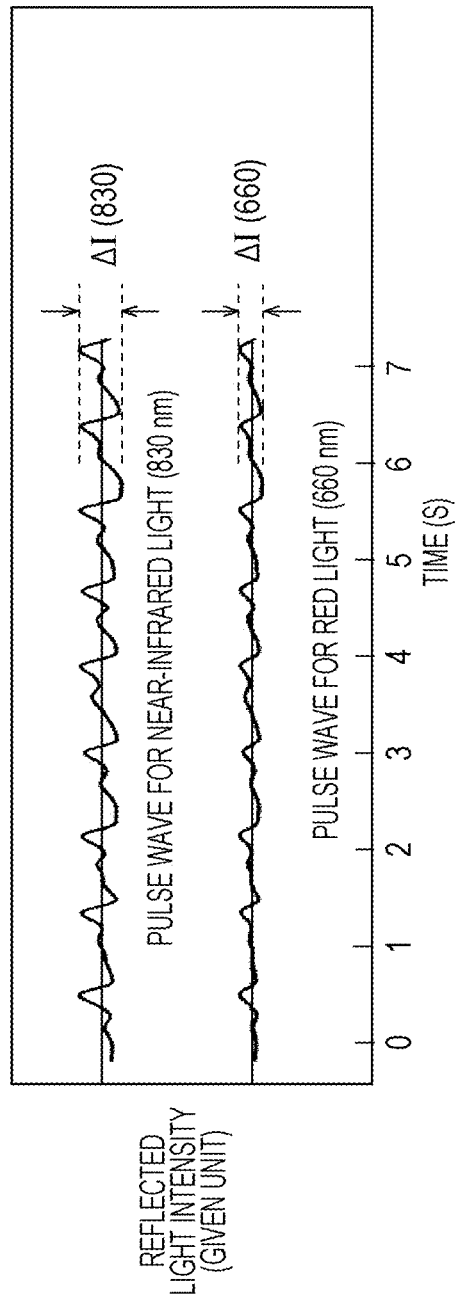
FIG. 11 is a diagram illustrating examples of pulse waves measured by using a method according to the fourth embodiment.

FIG. 11 is a diagram illustrating an example of temporal changes in the obtained scattered reflected light intensities. The reflected light intensity fluctuates over time for both near-infrared light (wavelength of 830 nm) and red light (wavelength of 660 nm). Here, let li(830) and li(660) respectively denote an intensity of light emitted from the light source 101 and an intensity of light emitted from the light source 102 at the living-body surface 4, and let Δl(830) and Δl(660) each denote an average of the fluctuation component of the scattered reflected light from the living body 3 over time. Blood oxygen saturation $SpO_2$ is calculated using Equation below.

$$SpO_2 = a + b*(\log(\Delta l(660)/li(660))/(\log(\Delta l(830)/li(830))),$$

where a and b can be decided upon based on a relationship with measured values obtained by an existing pulse oximeter.

To check the accuracy of the measuring instrument, oxygen saturation at a fingertip instead of the forehead is measured using the system according to the fourth embodiment. Specifically, oxygen saturation at a fingertip is measured while blood flow is stopped by pressuring the forearm at a certain pressure (200 mmHg) using a belt (cuff) used to measure the blood pressure.

For comparison, a commercially available pulse oximeter to which a finger is inserted is attached to the index finger. Oxygen saturation at the middle finger is measured in a non-contact manner by using the system according to the fourth embodiment. The above values a and b are decided upon by the first measurement, and blood oxygen saturation $SpO_2$ is measured by the second and subsequent measurements.

Figure 12:
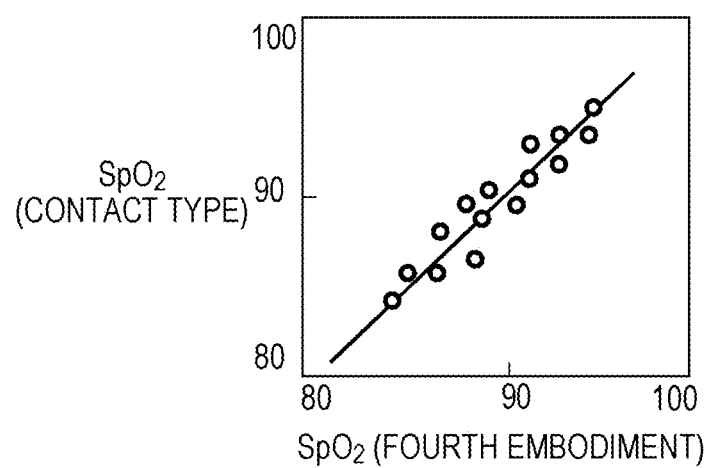
FIG. 12 is a diagram illustrating results obtained by measuring blood oxygen saturation by using the method according to the fourth embodiment and a method of the related art.

FIG. 12 illustrates a comparison result of the measured values obtained using the contact-type pulse oximeter and measured values obtained in accordance with the fourth embodiment. Since both results substantially match, FIG. 12 indicates that measurement is performed accurately. In the method of the fourth embodiment, not only blood oxygen saturation but also heart rate can be simultaneously measured based on the pulse waves illustrated in FIG. 11.

It is known that stress and tiredness can be measured from the fluctuation or a frequency characteristic of the pulse wave. The use of the system according to the fourth embodiment makes it possible to estimate a mental condition, such as stress, and a physical condition of a subject from the pulse wave in a non-contact manner.

Fifth Embodiment

A method for measuring blood oxygen saturation by using a single camera will be described as a fifth embodiment. In fourth embodiment, two cameras are used and signals for the light sources with different wavelengths are obtained by the respective cameras. This method has an advantage in that existing cameras can be used. However, since images are captured by controlling two cameras to operate together, the configuration of the system becomes complex. Also, since the obtained data is individual pieces of video data for the two cameras, synchronized data processing becomes complex. To avoid such complexities, in the fifth embodiment, a camera capable of simultaneously obtaining data of images for two wavelengths is implemented.

Figure 13:
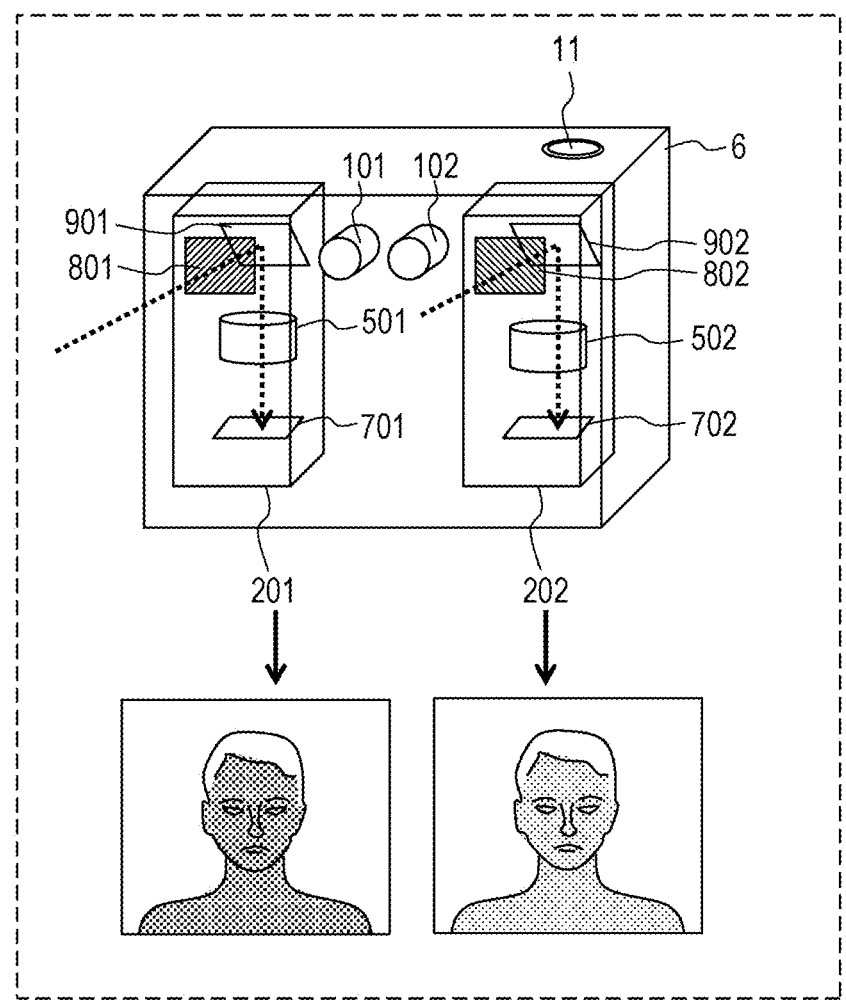
FIG. 13 is a diagram illustrating a configuration of a stereo-camera-type biological information detection device according to the fourth embodiment.

FIG. 13 is a diagram illustrating a configuration of a biological information detection device according to the fifth embodiment. This biological information detection device has a structure of a twin-lens stereo camera including two image capturing devices 201 and 202. Accordingly, herein, such a configuration is referred to as a "stereo camera configuration". The biological information detection device, which is a camera, includes a light source 101 (wavelength of 830 nm), which is a first laser point light source, and a light source 102 (wavelength of 760 nm), which is a second laser point light source. The light emitted by the light sources 101 and 102 and reflected by a living body 3 respectively passes through bandpass filters 801 and 802. Then, the propagating direction of the light is bent by mirrors 901 and 902 by 90 degrees, and images are formed on imaging surfaces of image sensors 701 and 702 via optical systems 501 and 502 (which include lenses), respectively. The bandpass filters 801 and 802 are narrow-band bandpass filters that pass only light having a wavelength of 830±15 nm and light having a wavelength of 760±15 nm that correspond to wavelengths of the two light sources 101 and 102, respectively.

In response to pressing of a shutter button 11, the two light sources 101 and 102 switch on, and the image sensors 701 and 702 simultaneously obtain images of the living body 3. The obtained images are converted into images of a stereo-image format by an image processing processor (corresponding to the first arithmetic circuit 22 or the second arithmetic circuit 23 in FIG. 3B), are subjected to image signal processing, and are accumulated in a storage device (corresponding to the memory 25 in FIG. 3B). The following processing is substantially the same as that of the third or fourth embodiment.

According to the fifth embodiment, by configuring an image capturing system as a single stereo camera, the entire system becomes compact, and the configuration of the following signal processing system from image signal processing to calculation of oxygen saturation can be simplified. In this way, a simple and fast operation can be implemented.

For example, 760 nm and 830 nm, which are in a near-infrared range, can be used as wavelengths of the two light sources. Since a difference in absorbance between oxyhemoglobin and deoxyhemoglobin is larger for 660 nm used in the fourth embodiment than that for 760 nm, oxygen saturation can be measured more accurately for the wavelength of 660 nm. However, since the wavelength of 660 nm is in a visible light range, the use of this wavelength may impose a load on the subject. Further, since light of a fluorescent lamp and a light-emitting diode (LED) illumination contains a component of the wavelength of 660 nm, measurement is easily affected by ambient light. In the fifth embodiment, the wavelength of 760 nm is selected in consideration of such issues. Since an absorbance peak of deoxyhemoglobin is at 760 nm, it is effective to use a wavelength of 760 nm to 780 nm if the wavelength of the light source having a shorter wavelength is set in the near-infrared range. The wavelengths used are not limited to the above ones, and may be appropriately selected in accordance with the usage and the use environment.

Sixth Embodiment

Another method for measuring blood oxygen saturation by using a single camera will be described as a sixth embodiment. In the fifth embodiment, the stereo camera configuration in which a single camera includes two optical systems and two image sensors is employed. In the sixth embodiment, a system is employed which obtains two different images corresponding to two wavelengths with a single image sensor by dividing an image using a plurality of lenses. The configuration according to the sixth embodiment is referred to as a "stereo lens configuration". The system of the stereo lens configuration will be described with reference to FIG. 14.

Figure 14:
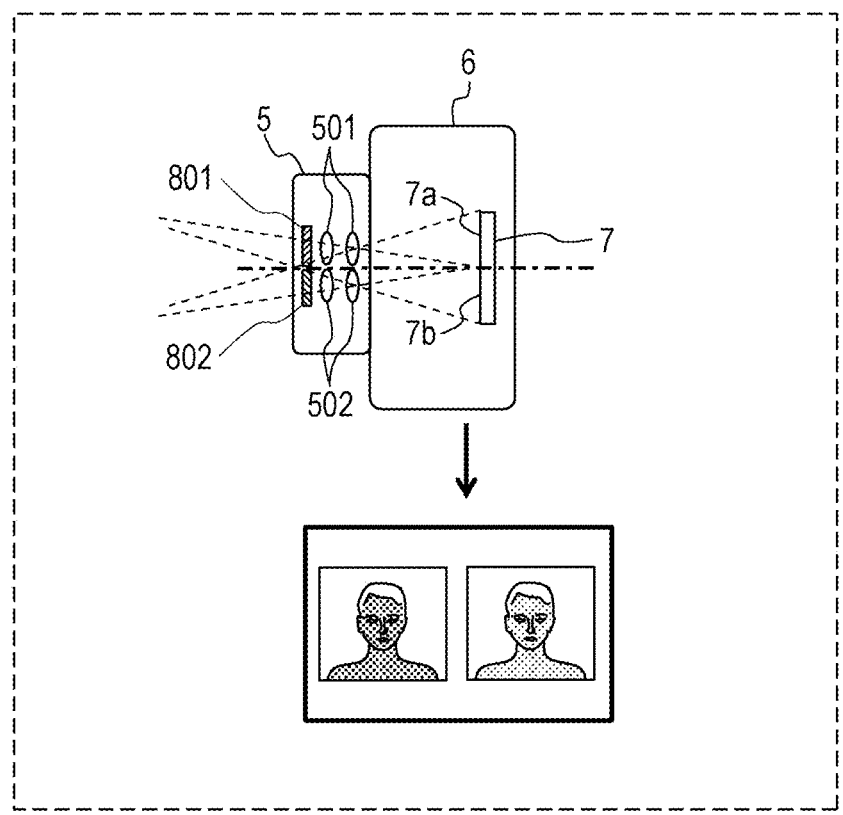
FIG. 14 is a diagram illustrating a configuration of a stereo-lens-type biological information detection device according to a fifth embodiment.

FIG. 14 is a cross-sectional view schematically illustrating a part of a biological information detection device according to the sixth embodiment. Although not illustrated in FIG. 14, the biological information detection device includes, for example, in a camera casing 6, two light sources that project dot patterns formed by light having two wavelengths of 830 nm and 760 nm. As illustrated in FIG. 14, an optical system 5 includes two optical systems 501 and 502 which are two sets of lenses. The optical systems 501 and 502 are designed to form respective images at two different regions on the imaging surface of the image sensor 7. Two narrow-band bandpass filters 801 and 802 that pass light having 830 nm and 760 nm corresponding to the wavelengths of the two light sources are disposed in front of the optical systems 501 and 502, respectively.

With such a configuration, two images based on light having two wavelengths for the same time point can be obtained by using a single image sensor 7. The second arithmetic circuit 23 calculates blood oxygen saturation from the two images by using the method similar to that of the third to fifth embodiments. According to the sixth embodiment, since a single image signal include information concerning two images corresponding to two different wavelengths for the same time point, the arithmetic processing becomes easier.

A result obtained by performing stress sensing by using the system of this stereo lens configuration will be described below. Japanese Unexamined Patent Application Publication Nos. 6-54836 and 2008-237244 disclose methods for detecting, with thermography, a decrease in temperature at a nose portion due to stress (nervousness) or concentration has been proposed. The blood flow decreases at the nose portion due to a psychological change, and in response to the decrease in the blood flow, temperature decreases at the nose portion. Methods for detecting such a temperature change with thermography are commonly carried out. A change in temperature at the face is caused by a change in blood flow. If a change in blood flow can be measured at a high accuracy, stress sensing can be implemented that is more accurate and more responsive than in the case of measuring a change in the surface temperature, which occurs as a result of a change in blood flow.

Figure 15A:
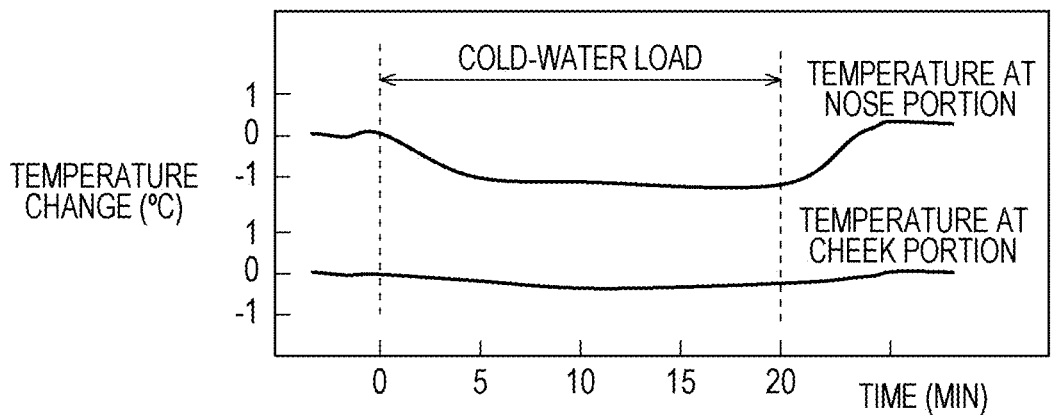
FIG. 15A is a diagram illustrating a result obtained by performing stress sensing by using a biological information detection device according to a sixth embodiment.

FIG. 15A is a diagram illustrating a result of stress sensing performed using the biological information detection device according to the sixth embodiment. A cold-water load for immersing the right hand into cold water (ice water) is imposed as stress. For comparison, a temperature change is measured using thermography at a nose portion and a cheek portion enclosed by dotted lines in FIG. 15B. FIG. 15A illustrates results of this measurement. The temperature at the nose portion gradually decreases in about three minutes after the cold-water load is started to be imposed and becomes stable after decreasing by approximately 1.2° C. FIG. 15A indicates that temperature returns to the original level in about three minutes after the load is removed. In contrast, temperature at the cheek portion is hardly affected by the cold-water load and is stable.

Figure 15B:
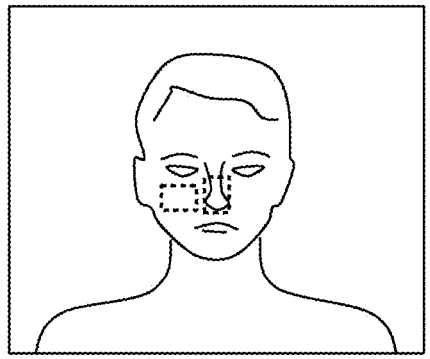
FIG. 15B is a diagram illustrating a nose portion and a cheek portion in an image in accordance with the sixth embodiment.
Figure 15C:
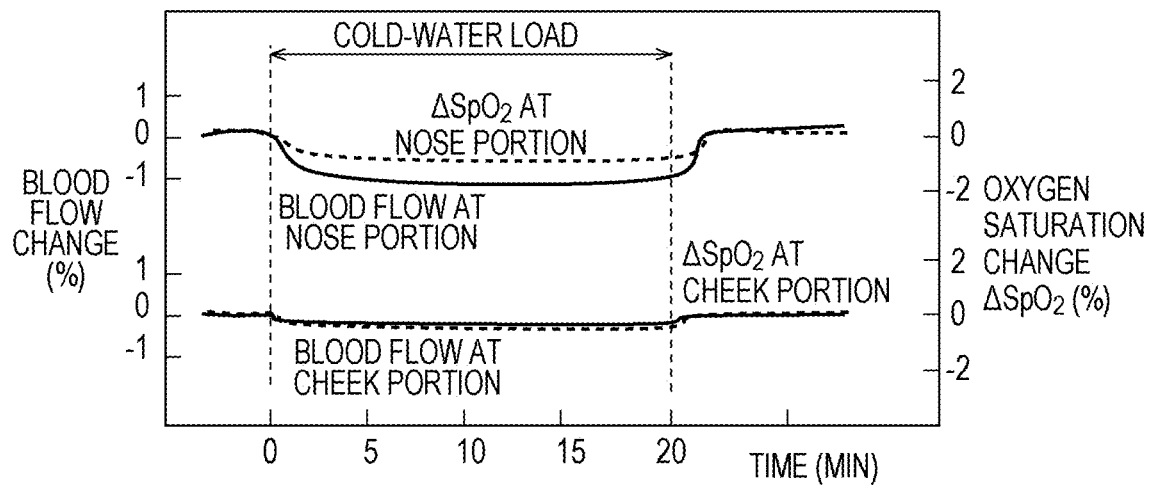
FIG. 15C is a diagram illustrating a change in blood flow and a change in blood oxygen saturation that are obtained by using the biological information detection device according to the sixth embodiment.

FIG. 15C is a diagram illustrating a change in blood flow and a change in blood oxygen saturation that are obtained by using the biological information detection device according to the sixth embodiment that employs the stereo lens configuration. Data for regions corresponding to the nose portion and the cheek portion, which are denoted by dotted-lines in FIG. 15B, are extracted from data of the blood flow and the oxygen saturation ($SpO_2$) at the face. A solid line denotes a change in the blood flow over time, whereas a dotted line denotes a change in the oxygen saturation ($\Delta SpO_2$) over time. As illustrated in FIG. 15C, the blood flow tends to decrease at the nose portion immediately after a cold stimulus is started, which indicates the responsivity with respect to time is high. In contrast, the blood flow hardly changes at the check portion. A decrease in the oxygen saturation is observed at the nose portion in response to a decrease in the blood flow, whereas the oxygen saturation hardly changes at the cheek portion.

As is apparent from the results, many pieces of data can be obtained by measuring blood flow and oxygen saturation at different portions of the face. An emotion, a physical condition, and a concentration degree can be detected at a high accuracy based on these pieces of data. The change in blood flow due to influence of the autonomic nervous system differs from portion to portion of the face. Thus, it is especially important to measure a change in blood flow at a specific portion by using a camera. At that time, the accuracy of the measurement can be increased by performing, at the same time, measurement at a portion where blood flow hardly changes and using the result as a reference.

Seventh Embodiment

Another method for measuring blood oxygen saturation by using a single camera will be described as a seventh embodiment.

Figure 16:
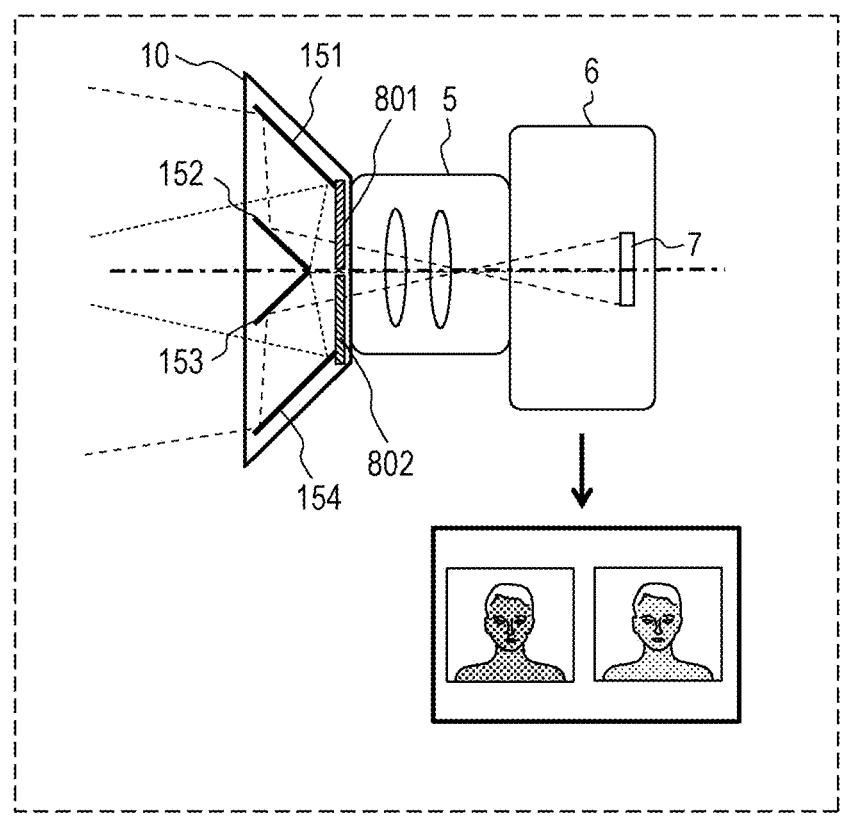
FIG. 16 is a cross-sectional view schematically illustrating a configuration of a biological information detection device according to a seventh embodiment.

FIG. 16 is a sectional view schematically illustrating a configuration of a biological information detection device according to the seventh embodiment. The biological information detection device includes a stereo adapter 10 attachable to an optical system 5, which includes ordinary lenses. The stereo adapter 10 is an attachment including four mirrors 151, 152, 153, and 154 and two bandpass filters 801 and 802. The use of the stereo adapter 10 allows two images corresponding to two wavelengths to be formed at two different regions on the imaging surface of an image sensor 7. This configuration is referred to as a "stereo adapter configuration".

In the stereo adapter configuration, two different images corresponding to two wavelengths can be obtained by a single image sensor 7 by using two sets of facing mirrors. Although not illustrated in FIG. 16, two light sources that respectively emit light having two wavelengths of 830 nm and 760 nm are included in a camera casing 6. The stereo adapter 10 is attached to an end of the optical system 5. The two sets of mirrors (a set of mirrors 151 and 152 and a set of mirrors 153 and 154) bend the light path twice to guide the light to the optical system 5. The narrow-band bandpass filters 801 and 802 that respectively pass light having the wavelengths of 830 nm and 760 nm corresponding to the wavelengths of the light sources are disposed between the optical system 5 and the mirrors 151, 152, 153, and 154.

This biological information detection device is able to obtain images of two wavelengths for the same time point by using a single image sensor 7. The basic concept is the same as that of the sixth embedment. Since the stereo lens configuration can make the optical system small, the entire system can be advantageously made small. In contrast, with the stereo adapter configuration, the entire system becomes larger but a powerful camera lens can be used and the resolution can be improved. Also, lenses of different magnifications and zoom lenses can be used. The stereo adapter configuration advantageously increases the degree of freedom of the system.

A study for detecting an emotion of a person by using the biological information detection device according to the seventh embodiment has been carried out. As described in the sixth embodiment, a feeling or emotion such as stress of a person can be stably detected based on blood flow. In response to a change in a feeling or emotion of a person, the autonomic nervous system becomes more active and blood flow on the skin surface changes. As a result of this change in blood flow, facial color changes. People detect an emotion or a physical condition of a target person from a subtle change in facial color without any difficulty. It is considered that a reason why a great doctor can diagnose a patient's physical condition and a cause of a disease by just looking at the patient's face is that such a doctor can identify a physical change from the subtle change in color of the patient's face. In addition, it is said that, when a person who is good at reading the situation reads a feeling of a counterpart, a subtle change in facial color as well as a subtle change in facial expression play an important role. Further, to make a situation natural and real in fields showing remarkable progresses recently, such as game, animation, and computer graphics, studies for subtly changing the facial color of a human character are widely carried out. As is apparent from these examples, the facial color represents an emotion and a physical condition of a person, and an attempt to read a feeling by measuring the facial color has been studied (see, for example, Kuroda and one other, "Analysis of facial color and skin temperature in emotional change and its synthesis of facial color", Human interface 1(1), pp. 15-20, Feb. 16, 1999). However, such an attempt to directly measure an emotion from facial color is not suitable for practical use because stable measurement is difficult. This is because a change in facial color differs from person to person and a change in facial color is subtle and is strongly influenced by disturbance light and a camera. Thus, stable measurement is difficult. A method for stably and highly accurately detecting an emotion by a measure other than measuring a change in facial color is desired.

It is known that facial color of a person is mainly decided by an amount of melanin contained in the skin surface (dermis) and concentrations of hemoglobin (oxyhemoglobin and deoxyhemoglobin) in blood. Since the amount of melanin does not fluctuate in a short time (changes due to a factor such as aging or tanning), a change in emotion can be stably measured by measuring blood flow. In the seventh embodiment, instead of measuring facial color, blood flow of oxyhemoglobin and deoxyhemoglobin that change the facial color is directly measured to detect a change in emotion. As described in the sixth embodiment, a change in blood flow differs from portion to portion of the face because an impact of the influence of the autonomic nervous system differs from portion to portion of the face. For example, the nose portion is easily influenced by the autonomic nervous system because lots of arteriovenous anastomosis is located at the nose portion, whereas the forehead portion is hardly influenced by a skin blood vessel contraction nerve. The second arithmetic circuit 23 according to the seventh embodiment determines blood flows at a plurality of different portions by computation and compares the obtained blood flows with each other, thereby being able to detect a change in emotion at a high accuracy.

Figure 17A:
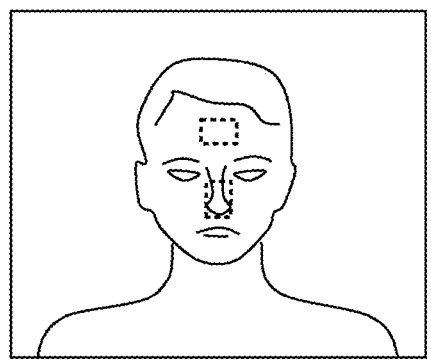
FIG. 17A is a diagram illustrating a nose portion and a forehead portion in an image in accordance with the seventh embodiment.

Measurement of a change in blood flow in response to an emotional change will be described below. The camera of the stereo adapter configuration illustrated in FIG. 16 is used to measure blood flow. A subject sits in front of the camera, and an image of the subject's face is captured with the camera. Color images of the face of the subject are obtained while showing the subject a video image that induces, from the secured state, feelings such as fear, laughter, surprise, and disgust. An emotional change is read based on a change in scene in the video image and the facial change in the color images, and a change in blood flow at the time of such a change is measured. Blood flow is measured at the nose portion and the forehead portion as indicated by dotted lines in FIG. 17A.

Figure 17B:
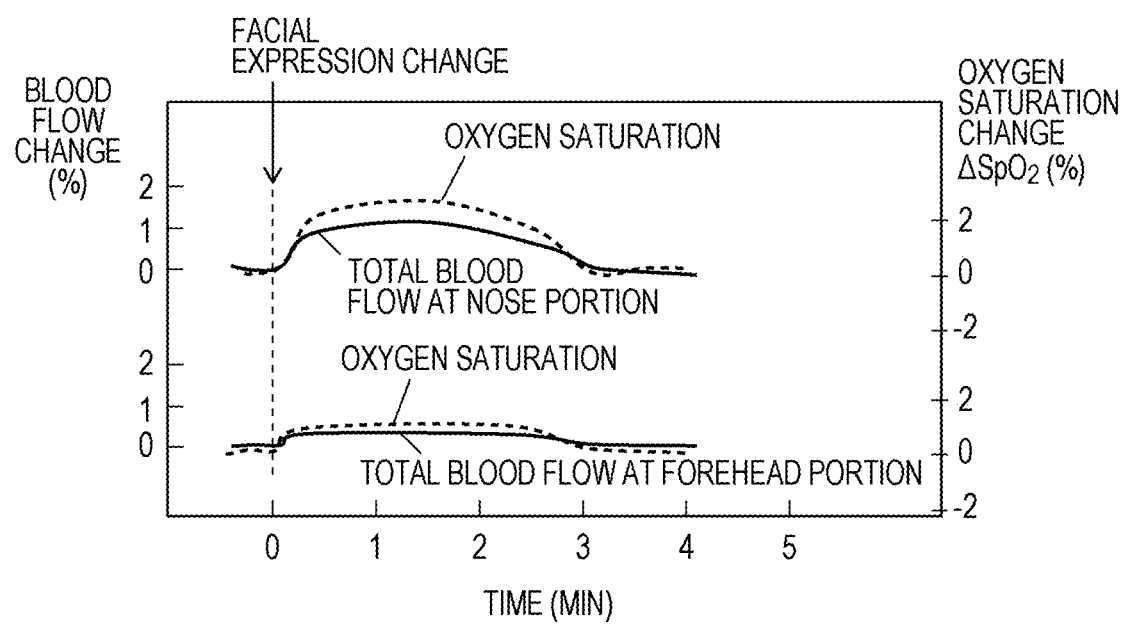
FIG. 17B is a diagram illustrating a temporal change in total blood flow (oxyhemoglobin and deoxyhemoglobin) and a temporal change in oxyhemoglobin blood flow (oxygen saturation) when an emotion of laughter is induced in accordance with the seventh embodiment.
Figure 18:
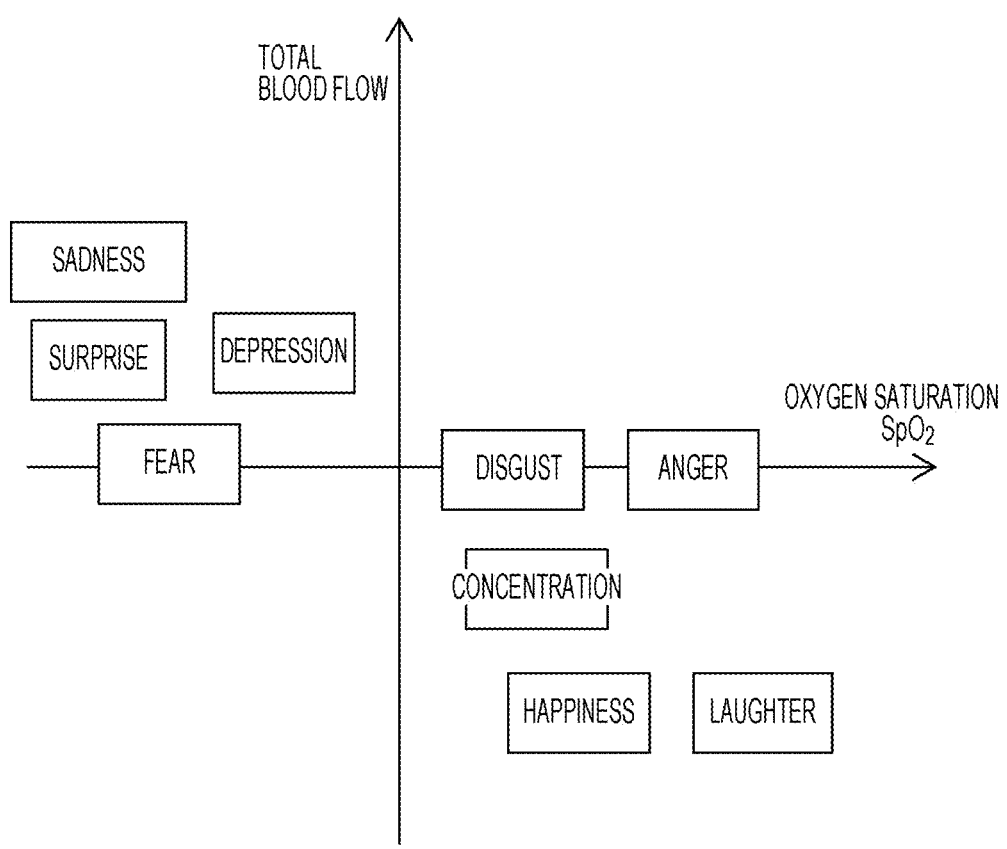
FIG. 18 is a diagram illustrating a relationship among emotions, total blood flow, and blood oxygen saturation.

FIG. 17B is a diagram illustrating a change in total blood flow (oxyhemoglobin and deoxyhemoglobin) over time and a change in the percentage of oxyhemoglobin blood flow (oxygen saturation) over time when an emotion causing laughter is induced. FIG. 17B indicates that the value of the total blood flow and the value of the blood oxygen saturation greatly change in response to the emotional change causing laughter. Similar examinations are performed for other emotions. FIG. 18 illustrates the result. FIG. 18 is a diagram obtained by plotting a relationship between blood flow and oxygen saturation that occurs in response to each emotional change by setting oxygen saturation as the horizontal axis and setting the total blood flow as the vertical axis. A change in the total blood flow and a change in the blood oxygen saturation are determined by calculation for the case where emotions other than laughter, such as sadness, surprise, depression, fear, disgust, anger, concentration, and happiness, are induced. The same measurement is performed for twelve subjects. FIG. 18 illustrates the average of the experiment results obtained for the twelve subjects. Although there is a variation among individuals, the change in the total blood flow and the change in the blood oxygen saturation have showed the similar tendencies for almost all the subjects. This result indicates that an emotional change can be detected from at least one of blood flow and oxygen saturation.

As illustrated in FIG. 17B, a relationship between oxygen saturation and blood flow differs from portion to portion of the face. Accordingly, highly accurate emotion sensing can be performed by determining blood flow and oxygen saturation at a plurality of portions of the face. In the emotion sensing test performed in the seventh embodiment, measurement is performed at three portions, i.e., at the forehead, the cheek, and the nose. A change in oxygen saturation and a change in blood flow in response to an emotional change differ among the forehead, the cheek, and the nose. Accordingly, an emotional change can be detected highly accurately by creating in advance a table indicating a relationship between a change in oxygen saturation and a change in blood flow at each portion and calculating a correlation with the actually measured values of oxygen saturation and blood flow.

Eighth Embodiment

A method for measuring blood oxygen saturation by using a single camera without dividing an image by an optical system will be described as an eighth embodiment. In the third to seventh embodiments, the methods for dividing light from two light sources corresponding to two wavelengths, performing sensing, and determining biological information, such as oxygen saturation, by computation have been described. A biological information detection device according to the eighth embodiment obtains, with an image sensor, two image signals for different wavelengths without dividing an image.

Figure 19A:
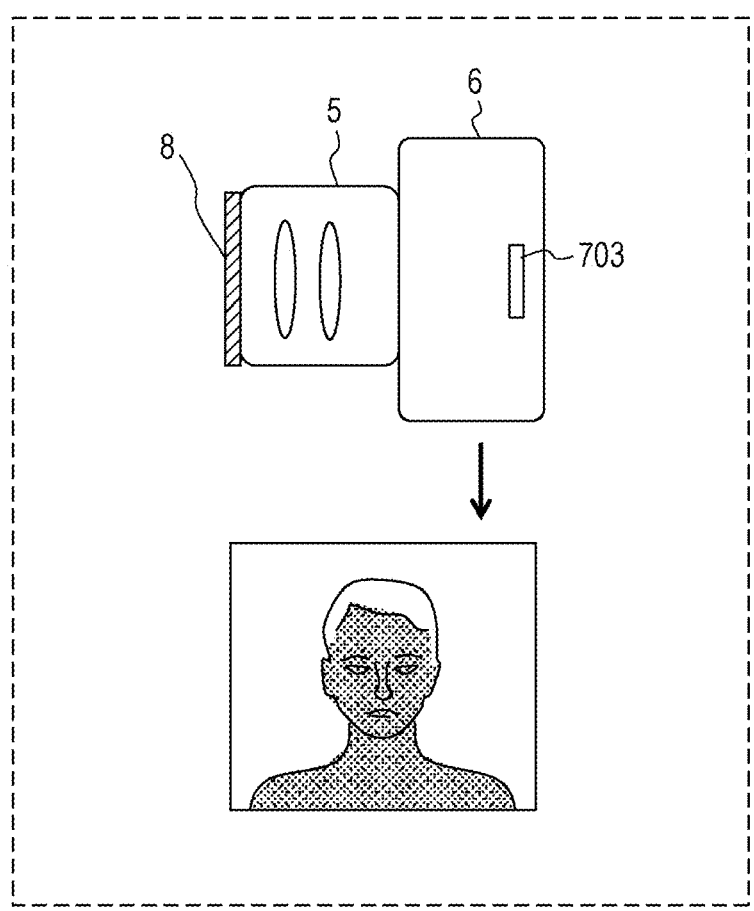
FIG. 19A is a diagram schematically illustrating a configuration of a biological information detection device according to an eighth embodiment.

FIG. 19A is a diagram schematically illustrating a configuration of the biological information detection device according to the eighth embodiment. This biological information detection device separates two images corresponding to two wavelengths by using an image sensor 703 instead of by using the optical system. Although illustration of point light sources is omitted in FIG. 19A, two light sources that respectively emit light having a wavelength of 830 nm and light having a wavelength of 760 nm are included in a camera casing 6. A bandpass filter 8 that passes light having a wavelength longer than or equal to 730 nm and shorter than or equal to 850 nm is disposed in front of an optical system 5, which includes lenses, of the camera. The bandpass filter 8 cuts visible light and infrared light having long wavelengths. Light that has passed through the bandpass filter 8 forms an image on the imaging surface of the image sensor 703 via the optical system 5. Unlike ordinary image sensors, the image sensor 703 used in the eighth embodiment includes two kinds of bandpass filters that pass near-infrared light.

Figure 19B:
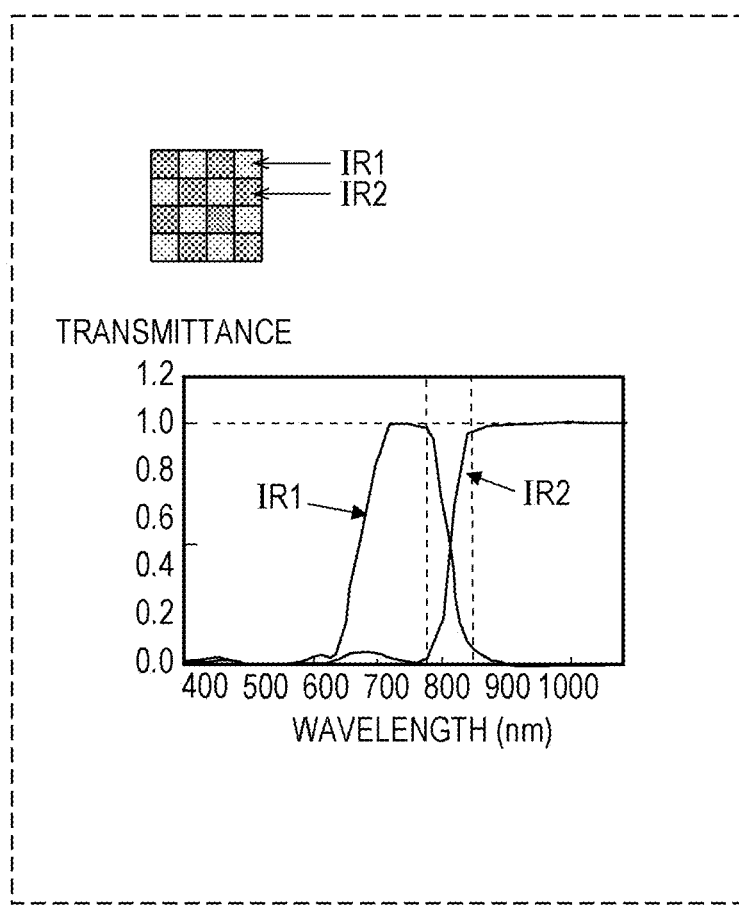
FIG. 19B is a diagram illustrating a plurality of color filters in accordance with the eighth embodiment.

FIG. 19B is a diagram illustrating a plurality of filters that face a plurality of photodetector cells disposed on the imaging surface of the image sensor 703. The image sensor 703 includes filters IR1 that selectively pass light having a wavelength of 680 nm to 800 nm and filters IR2 that selectively pass light having a wavelength of 800 nm or longer. The filters IR1 and IR2 are arranged in a checkered pattern. The lower image in FIG. 19B is a diagram illustrating an example of wavelength dependency of transmittance of the filters IR1 and IR2. The image sensor 703 detects, with a plurality of photodetector cells (also referred to as pixels), two images based on light having 760 nm and 830 nm which are wavelengths of the two light sources.

Figure 19C:
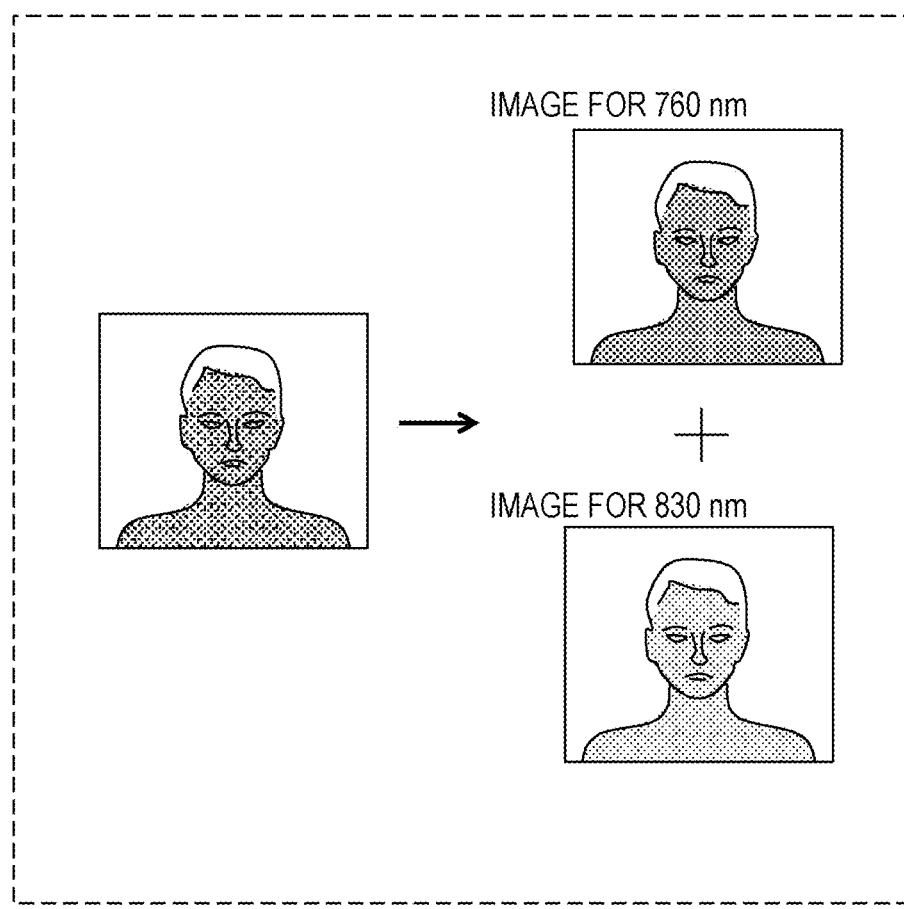
FIG. 19C is a diagram illustrating an example of images generated in accordance with the eighth embodiment.

The first arithmetic circuit 22 (FIG. 3B) separately reads data obtained by the plurality of photodetector cells of the image sensor 703 for the wavelength of 760 nm and data obtained by the plurality of photodetector cells for the wavelength of 830 nm. The first arithmetic circuit 22 detects a human body region in each of the images. As illustrated in FIG. 19C, the second arithmetic circuit 23 (FIG. 3B) then generates an image for the wavelength of 760 nm and an image for the wavelength of 830 nm by adding, to the corresponding data, data for lacking pixels by interpolation. The second arithmetic circuit 23 calculates blood flow and oxygen saturation from these two images. Since these two images completely coincide with each other, calculating blood flow and oxygen saturation from these images is easier than calculation using two different images. However, since the filtering performance of the filters is lower than that achieved in the case where bandpass filters corresponding to respective light sources are used, there is a concern about occurrence of color mixing between the light sources in this method.

Ninth Embodiment

A biological information detection device capable of obtaining not only two images corresponding light sources with two wavelength but also a color image without dividing an image will be described as a ninth embodiment.

Figure 20A:
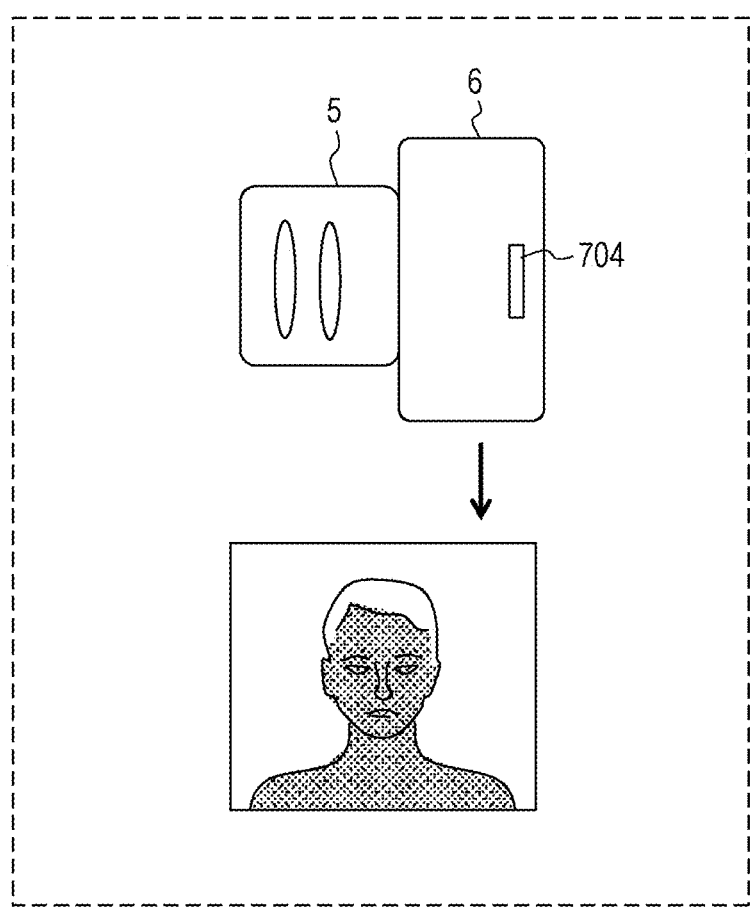
FIG. 20A is a diagram illustrating a configuration of a biological information detection device according to a ninth embodiment.

FIG. 20A is a diagram illustrating a configuration of the biological information detection device according to the ninth embodiment. Although illustration of point light sources is omitted also in FIG. 20A, two light sources that respectively emit light having a wavelength of 830 nm and light having a wavelength of 760 nm are included in a camera casing 6. In the ninth embodiment, to obtain a color image, no bandpass filter is disposed in front of an optical system 5, which includes lenses. Visible light and light emitted by the leaser light sources form images on an imaging surface of an image sensor 704 via the optical system 5. Unlike ordinary image sensors, the image sensor 704 used in the ninth embodiment includes photodetector cells that obtain a color image and two kinds of photodetector cells that obtain near-infrared images.

Figure 20B:
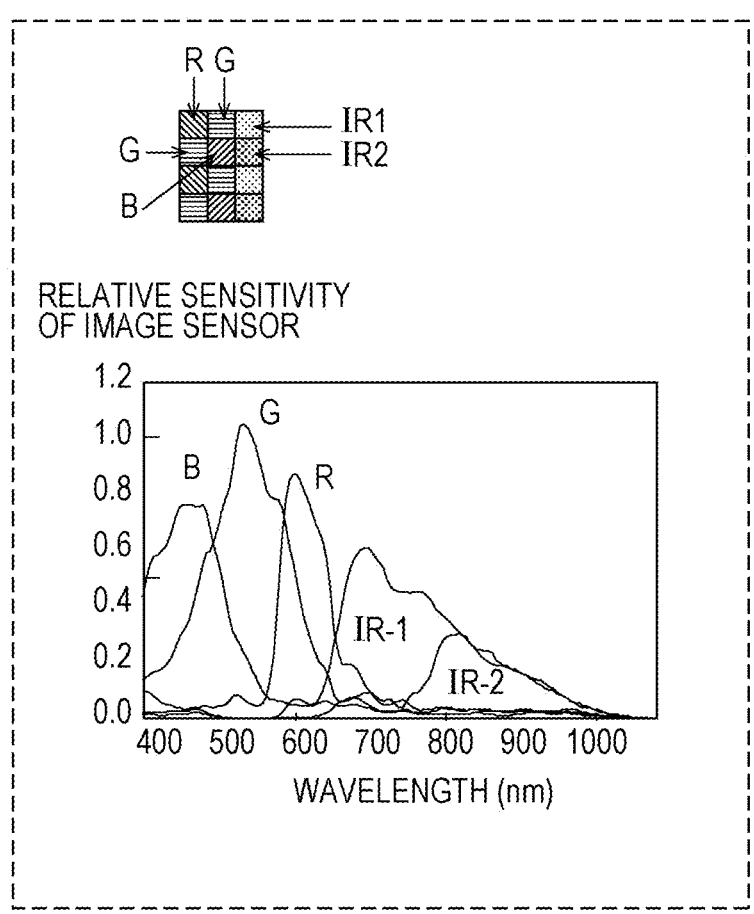
FIG. 20B is a diagram illustrating a plurality of color filters in accordance with the ninth embodiment.

FIG. 20B is a diagram illustrating a plurality of bandpass filters (or color filters) disposed on the imaging surface of the image sensor 704. The lower image in FIG. 20B illustrates wavelength dependencies of relative sensitivities of pixels that face corresponding filters. As illustrated in FIG. 20B, three types of color filters (R, G, and B filters) that respectively pass red light, green light, and blue light, filters IR-1 that pass light having 650 nm or longer, and filters IR-2 that pass light having 800 nm or longer are arranged on the imaging surface. An array in which two G filters are disposed diagonally adjacent to each other and R and B filters are disposed on the opposite diagonal side is the same as the Bayer array of ordinary image sensors. This image sensor 704 differs from ordinary image sensors in that two filters IR-1 and IR-2 are arranged next to a basic unit of four filters arranged in the Bayer array.

Figure 20C:
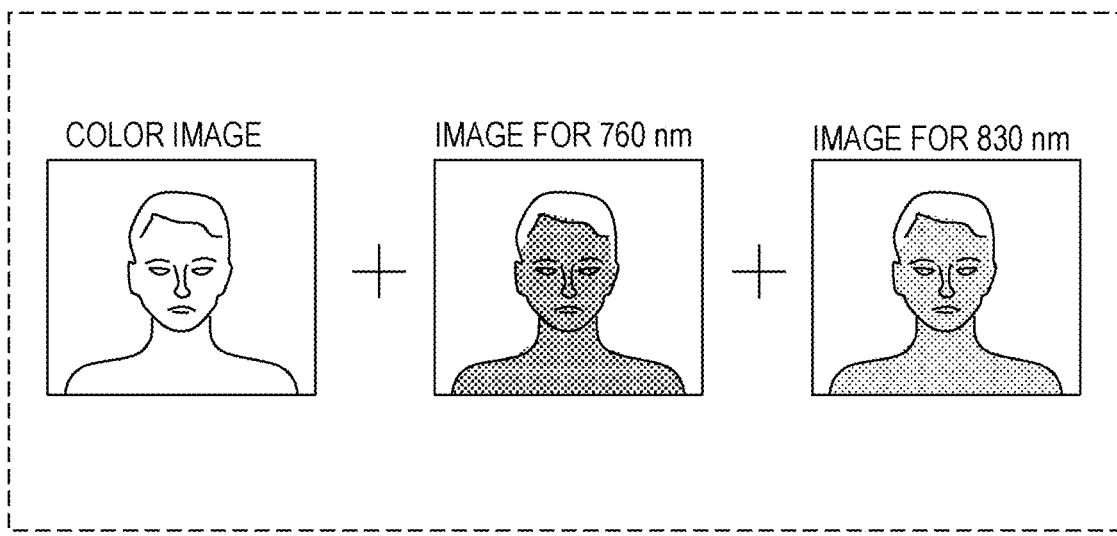
FIG. 20C is a diagram illustrating an example of images generated in accordance with the ninth embodiment.

The filter IR1 of the eighth embodiment and the filter IR-1 of the ninth embodiment have different transmission wavelength ranges. The filter IR1 of the eighth embodiment is a relatively narrow-band filter that passes light having a wavelength range from 650 nm to 800 nm. In contrast, in the ninth embodiment, a filter that passes light having a wavelength range of 650 nm or longer is used to simplify the manufacturing process of the image sensor 704. However, the configuration is not limited to this one, and the filter described in the eighth embodiment can also be used. The filter IR-1 of the ninth embodiment is sensitive to both 760 nm and 830 nm. Accordingly, the second arithmetic circuit 23 calculates a signal corresponding to 760 nm by subtracting the signal of the photodetector cells that face the filter IR-2 from the signal of the photodetector cells that face the filter IR-1 and then determines blood oxygen saturation. Consequently, an image (color image) of red, blue, and green, an image for the wavelength of 760 nm, and an image for the wavelength of 830 nm are determined by the image sensor 704 as illustrated in FIG. 20C.

In this configuration, color mixing is more likely to occur than in the eighth embodiment. However, a color image and information regarding blood flow and blood oxygen saturation can be simultaneously obtained by the simple system using a single camera. An advantage of this system is that visible-light-based images without parallax and near-infrared images can be obtained since a single camera is used to capture visible-light-based images and near-infrared images. This is particularly effective in usages in which a visible-light-based image and near-infrared images are superimposed for display.

Figure 20D:
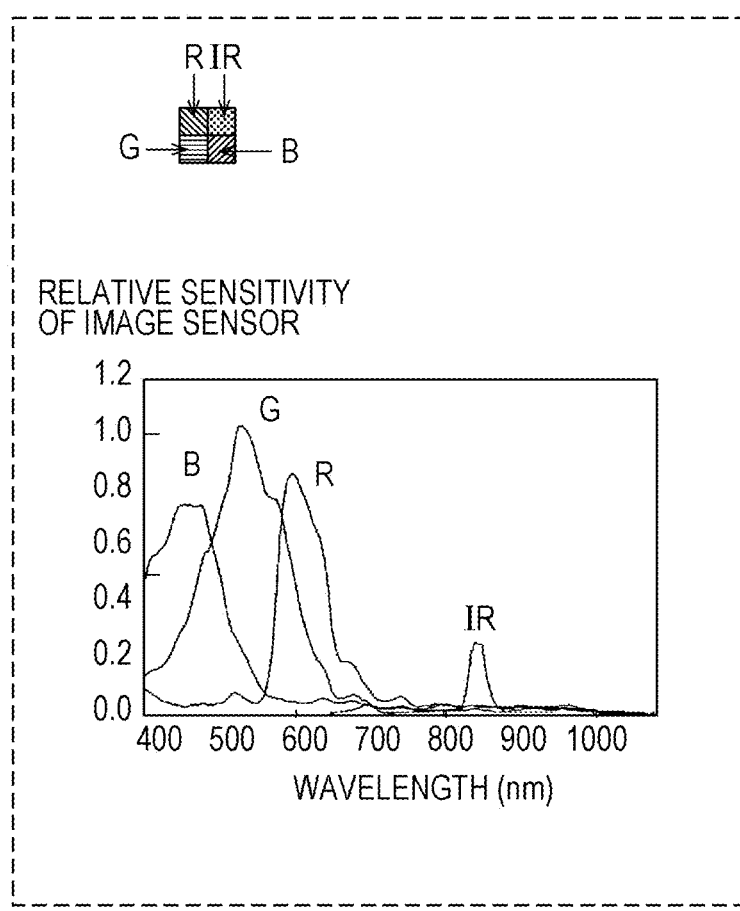
FIG. 20D is a diagram illustrating an example of a configuration of a multi-spectral sensor including four types of color filters for red (R), green (G), blue (B), and infrared (IR) light.

In the ninth embodiment, an example of a configuration of a biological information sensing camera that uses a multi-spectral sensor that support five wavelengths including two wavelengths in an infrared range and three wavelengths (red, blue, and green) in a visible light range has been described. With the human body detection camera described in the first embodiment, capturing of a color image and human body detection can be performed through measurement on four wavelengths including one wavelength in an infrared range and three wavelengths (red, blue, and green) in a visible light range. The multi-spectral sensor (illustrated in FIG. 20D, for example) having four types of color filters corresponding to four wavelengths is usable for such a purpose. A color filter is disposed such that a near-infrared (IR) pixel is assigned to one pixel out of two green pixels of the Bayer array that is commonly used in the image sensor. In the ninth embodiment, a camera for a system that switches on a near-infrared illumination of 850 nm is assumed, and a filter that selectively passes the wavelength of 850 nm is selected as a near-infrared filter. The use of such a camera makes it possible to use a single camera system as an ordinary color camera and a living body detection camera. Consequently, only one surveillance camera is needed, and it is easier to extract a color image of a portion in which a person is detected than in the case where two cameras are used. In the ninth embodiment, a color filter for 850 nm is used; however, the near-infrared filter may be changed in accordance with the near-infrared light source used.

Other Embodiments

While the embodiments of the present disclosure have been described above by way of example, the present disclosure is not limited to the above embodiments and can be variously modified. The process described in each of the above embodiments may be applied to other embodiments. Examples of the other embodiments will be described below.

In the embodiments above, laser light sources are used as the array point light sources; however, light sources of other types may be used. For example, less costly LED light sources may be used. However, light emitted by the LED light source has a lower straightness than that emitted by the laser light source and is more likely to spread. Accordingly, when LED light sources are used, a dedicated condensing optical system may be used or a distance between an image-capturing target and a camera may be limited.

The biological information detection device may include an adjustment mechanism that adjusts focus of the optical system. Such an adjustment mechanism can be implemented by, for example, a motor (not illustrated) and the control circuit 26 illustrated in FIG. 3B. Such an adjustment mechanism adjusts focus of the optical system to maximize contrast of a dot pattern image projected onto a target by the light source. With this configuration, accuracy of calculation of contrast described in the first embodiment improves.

The first arithmetic circuit 22 detects a living body region by using an image signal output from an image sensor. If a plurality of living body regions (a face region and a hand region of different persons or the same person) are detected in the image at that time, the first arithmetic circuit 22 may select a living body region that should be detected, on the basis of the size or shape of the detected regions.

The second arithmetic circuit 23 may generate information concerning the epidermis including information concerning at least one of a melanin concentration, presence or absence of a spot, and presence or absence of a bruise on the basis of the image signal. As described above, the epidermis contains melanin that strongly absorbs light. A spot and a bruise are caused as a result of an increase in melanin. Accordingly, a melanin concentration, a spot, and a bruise can be detected based on an intensity distribution of light from the living-body surface. For example, the second arithmetic circuit 23 may extract, from the image signal, directly reflected light components from the surface of a living body and may generate information concerning the epidermis including information concerning at least one of a melanin concentration, presence or absence of a spot, and presence or absence of a bruise on the basis of the directly reflected light components. The directly reflected light components can be obtained by determining whether contrast exceeds a predetermined threshold as in the first embodiment or by removing a low-frequency component from the image signal, for example.

In the present disclosure, the double camera configuration using two cameras (FIG. 8), the stereo camera configuration (FIG. 13) in which one camera includes two optical systems and two image sensors, the stereo lens configuration (FIG. 14) using two sets of lenses and one image sensor, the stereo adapter configuration (FIG. 16) using a lens adapter, one lens, and one image sensor, the configuration (FIG. 19A and FIG. 20A) that divides an image using the image sensor have been described. As already described, since each configuration has advantages and drawbacks, an appropriate configuration can be selected in accordance with the usage.

As described above, according to the embodiments of the present disclosure, not only heart rate and blood flow but also blood oxygen saturation can be measured without restraining a subject and without placing a detection device, such as a sensor, in contact with the subject. An emotion or a physical condition of the subject can also be estimated from measured values of blood flow and oxygen saturation at different portions of the subject.

What is claimed is:
1. A device comprising:
a light source that, in operation, projects dots onto a user's face, the dots being formed by first light;
a first photodetector that, in operation, detects second light resulting from the projection of the dots onto the user's face; and
one or more circuits, wherein
the one or more circuits, in operation, generate first information that is a depth of a surface of the user's face, based on positions of the dots on the surface of the user's face, and second information that is internal biological information of the user's face, based on the second light.
2. The device according to claim 1, wherein
the second information includes at least one piece of information selected from the group consisting of heart rate, blood pressure, and blood flow.
3. The device according to claim 1, wherein
the first information further indicates a depth-direction motion of the user's face.
4. The device according to claim 1, wherein
the one or more circuits perform an authentication of an individual, based on at least the second information.
5. The device according to claim 1, wherein
the one or more circuits determine, based on a shift in the positions of the dots, a presence or an absence of a relative motion of the user's face with respect to the device.
6. The device according to claim 1, wherein
the second light includes scattered light that is scattered inside the user's face, and
the one or more circuits, in operation, calculate the second information based on at least the scattered light.
7. The device according to claim 6, wherein
the scattered light exits from a portion of the user's face onto which none of the dots are projected.

8. The device according to claim 1, wherein
the first light has a wavelength longer than or equal to 650 nm and shorter than or equal to 950 nm.

9. The device according to claim 1 further comprising:
a second photodetector that detects visible light.

10. The device according to claim 1, wherein the one or more circuits
perform at least one piece of authentication selected from the group consisting of fingerprint authentication, iris authentication, and vein authentication.

11. The device according to claim 1, wherein the light source is an array point light source that projects a plurality of discretely arranged dot patterns onto the user's face.

12. The device according to claim 1, wherein the second light includes reflected light and scattered light.

13. The device according to claim 12, wherein the second information is obtained by spatially separating the reflected light and the scattered light.

14. A device comprising:
a light source that, in operation, projects dots onto a target, the dots being formed by first light;
a first photodetector that, in operation, detect second light resulting from the projection of the dots onto the target; and
one or more circuits, wherein
the one or more circuits, in operation,
generate information that is a depth of a surface of the target, based on positions of the dots on the target,
determine whether the target is a living body or not based on the second light,
perform a biometric authentication of the target, and
authenticate an individual, in response to a determination that the target is a living body and a result of the biometric authentication.

15. The device according to claim 14, wherein
the one or more circuits, in operation, determine whether the target is a human face or a duplicate of a human face.

16. The device according to claim 14, wherein
the second light includes:
reflected light that is reflected by the target; and
scattered light that exits from inside of the target after entering the inside of the target and being scattered, and
the one or more circuits, in operation, determine whether the target is a living body or not, based on the directly reflected light and the scattered light.

17. The device according to claim 14, wherein
the first light has a wavelength longer than or equal to 650 nm and shorter than or equal to 950 nm.

18. The device according to claim 14 further comprising:
a second photodetector that detects visible light.

19. The device according to claim 14, wherein the light source is an array point light source that projects a plurality of discretely arranged dot pattern onto the living body.

20. The device according to claim 14, wherein,
the one or more circuits, in operation, generate information that is a depth of a surface of the target, based on positions of the dots on the target.

* * * * *